(12) United States Patent
Farley et al.

(10) Patent No.: US 9,378,655 B2
(45) Date of Patent: Jun. 28, 2016

(54) ASSOCIATING USER EMOTION WITH ELECTRONIC MEDIA

(71) Applicant: QUALCOMM Incorporated, San Diego, CA (US)

(72) Inventors: Richard O. Farley, San Diego, CA (US); Robert S. Tartz, San Marcos, CA (US); Aniket A. Vartak, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 184 days.

(21) Appl. No.: 13/692,954

(22) Filed: Dec. 3, 2012

(65) Prior Publication Data

US 2014/0154649 A1 Jun. 5, 2014

(51) Int. Cl.
*G09B 19/00* (2006.01)
*A61B 5/00* (2006.01)
*A61B 5/16* (2006.01)

(52) U.S. Cl.
CPC ............... *G09B 19/00* (2013.01); *A61B 5/165* (2013.01); *A61B 5/6898* (2013.01)

(58) Field of Classification Search
CPC ............ G09B 19/00; G09B 5/02; G09B 5/06; A61B 5/165; A61B 5/0482; A61B 5/486
USPC ........................................................ 434/236
See application file for complete search history.

(56) References Cited

U.S. PATENT DOCUMENTS

| | | | |
|---|---|---|---|
| 5,261,747 A | 11/1993 | Deacutis et al. | |
| 6,032,062 A | 2/2000 | Nisch | |
| 6,293,904 B1 * | 9/2001 | Blazey | A61B 5/16 434/236 |
| 6,326,936 B1 | 12/2001 | Inganas et al. | |
| 7,233,684 B2 | 6/2007 | Fedorovskaya et al. | |
| 8,447,610 B2 * | 5/2013 | Meyer et al. | 704/260 |
| 2003/0088167 A1 | 5/2003 | Fendrock et al. | |
| 2004/0027474 A1 * | 2/2004 | Aoyama et al. | 348/335 |
| 2004/0039296 A1 | 2/2004 | Szopinski | |
| 2004/0117212 A1 * | 6/2004 | Kong et al. | 705/2 |
| 2006/0047187 A1 | 3/2006 | Goyal et al. | |

(Continued)

FOREIGN PATENT DOCUMENTS

| | | |
|---|---|---|
| EP | 1278064 A1 | 1/2003 |
| EP | 1407713 A1 | 4/2004 |

(Continued)

OTHER PUBLICATIONS

Sakurazawa, et al., "Entertainment Feature of a Game Using Skin Conductance Response," Proceedings of the 2004 ACM SIGCHI International Conference on Advances in computer entertainment technology [Online] 2004, pp. 181-186.

(Continued)

*Primary Examiner* — Sam Yao
*Assistant Examiner* — Jerry-Daryl Fletcher
(74) *Attorney, Agent, or Firm* — Charles E. Eggers

(57) ABSTRACT

Systems, methods, devices, and apparatuses for associating a user emotion with electronic media are described. Contact between a user of a device and a biopotential electrode array that is integrated with the device is detected. Electrodermal data of the user is acquired via the biopotential electrode array. The user emotion is derived based at least in part on the acquired electrodermal data. The user emotion is then associated with the electronic media.

36 Claims, 17 Drawing Sheets

(56) References Cited

U.S. PATENT DOCUMENTS

| | | |
|---|---|---|
| 2006/0057771 A1 | 3/2006 | Kovacs et al. |
| 2007/0027386 A1 | 2/2007 | Such et al. |
| 2007/0149876 A1 | 6/2007 | Mouradian et al. |
| 2007/0193887 A1 | 8/2007 | Tormoen et al. |
| 2008/0177190 A1 | 7/2008 | Libbus et al. |
| 2008/0235284 A1 | 9/2008 | Aarts et al. |
| 2009/0177144 A1 | 7/2009 | Masmanidis et al. |
| 2010/0036230 A1 | 2/2010 | Greene et al. |
| 2010/0041975 A1 | 2/2010 | Chen et al. |
| 2010/0086204 A1 | 4/2010 | Lessing |
| 2010/0123588 A1 | 5/2010 | Cruz et al. |
| 2011/0177481 A1* | 7/2011 | Haff et al. ............ 434/317 |
| 2011/0213268 A1 | 9/2011 | Kosaka et al. |
| 2012/0083675 A1 | 4/2012 | El Kaliouby et al. |
| 2012/0165622 A1 | 6/2012 | Rodr Guez Ib Nez et al. |
| 2012/0222057 A1 | 8/2012 | Sadowsky et al. |
| 2013/0085367 A1 | 4/2013 | Vartak et al. |
| 2013/0143185 A1* | 6/2013 | Liu et al. ............ 434/236 |
| 2013/0317318 A1 | 11/2013 | Tartz et al. |

FOREIGN PATENT DOCUMENTS

| | | |
|---|---|---|
| EP | 1685794 A1 | 8/2006 |
| GB | 2378762 A | 2/2003 |
| JP | H10201726 A | 8/1998 |
| JP | 2007190225 A | 8/2007 |
| JP | 2008541977 A | 11/2008 |
| JP | 2011530334 A | 12/2011 |
| JP | 2012509145 A | 4/2012 |
| WO | 2006090371 A2 | 8/2006 |
| WO | 2006131855 A2 | 12/2006 |
| WO | 2008017416 A2 | 2/2008 |
| WO | 2011022068 A1 | 2/2011 |
| WO | 2011094399 A2 | 8/2011 |

OTHER PUBLICATIONS

Boucsein "Generalized Psychophysiological States" Electrodermal Activity, New York, Plenum Press, Sec. 3.2, 1992, pp. 260-292.
Russell "A Circumplex Model of Affect", Journal of Personality and Social Psychology, vol. 39, No. 6, 1980, pp. 1161-1178.
International Search Report and Written Opinion—PCT/US2013/071443—ISA/EPO—Feb. 4, 2014.

* cited by examiner

ASSOCIATING USER EMOTION WITH ELECTRONIC MEDIA

BACKGROUND

Mobile devices and wireless communication systems are widely deployed to provide various types of electronic communication content such as voice, data, and so on. While electronic forms of communication (e.g., email, text messages, voicemail, phone calls, images, videos, audio recordings, and web pages) have enabled people to conveniently contact and interact with others, the richness of electronic communications is attenuated.

Electronic communications, by themselves, do not generally convey the full emotional state of the sender. For example, research suggests that a small amount of emotional context in a given message is conveyed by the words (e.g., text in an electronic communications). A greater amount of the emotional context is conveyed vocally by the tone of the voice. An even greater amount is expressed using non-verbal communication, such as facial expression and other body gestures. With regard to electronic communications, the emotional context or emotional state of the content creator or sender is commonly misinterpreted by the receiver.

SUMMARY

The described features generally relate to one or more improved systems, methods, devices, and/or apparatuses for associating a user emotion with electronic media. In accord with an example method, contact between a user of a device and a biopotential electrode array that is integrated with the device is detected. Electrodermal data of the user is acquired via the biopotential electrode array. The user emotion is derived based at least in part on the acquired electrodermal data. The user emotion is then associated with the electronic media.

A method of associating a user emotion with electronic media is described. Contact between a user of a device and a biopotential electrode array that is integrated with the device may be detected. Electrodermal data of the user may be acquired via the biopotential electrode array. The user emotion may be derived based at least in part on the acquired electrodermal data, and the user emotion may be associated with the electronic media.

In one embodiment, a capturing of the electronic media may be detected by the device. The contact between the user of the device and the biopotential electrode array may be detected at least partly in response to detecting the capturing. A play back of the electronic media may be detected by the device. The contact between the user of the device and the biopotential electrode array may be detected at least partly in response to detecting the play back. A presentation of the electronic media may be detected by the device. The contact between the user of the device and the biopotential electrode array may be detected at least partly in response to detecting the presentation. Further, activation of an application installed on the device may be detected. The contact between the user of the device and the biopotential electrode array may be detected at least partly in response to detecting the activation. In one example, the application is a camera application.

In one configuration, an orientation of the device with respect to gravity may be detected. The contact between the user of the device and the biopotential electrode array may be detected at least partly in response to detecting the orientation. The orientation may be a landscape orientation.

In one embodiment, acquiring the electrodermal data may include dynamically configuring the biopotential electrode array, based at least in part on the detected contact, and acquiring the electrodermal data from the configured biopotential electrode array. Dynamically configuring the biopotential electrode array may include electrically coupling at least two adjacent electrode tiles to form a first active electrode area within the biopotential electrode array.

In one example, deriving the user emotion may include correlating the electrodermal data with one of a plurality of emotional states. Associating the user emotion with the electronic media may include saving the user emotion as metadata of the electronic media. Associating the user emotion with the electronic media may further include saving the user emotion in a schema associated with the electronic media.

In one configuration, a user interface may be presented on the device to edit the user emotion. The electronic media may be an image. The electronic media may be a video. The electronic media may be an audio recording. In one example, the device may be a mobile phone. The device may be a camera.

In one embodiment, the biopotential electrode array may include a group of electrodes positioned at a corner of the device, on at least a side edge of the device. The biopotential electrode array may include a plurality of groups of electrodes, each group of electrodes being positioned at a different one of four corners of the device, and each group of electrodes being positioned on at least a side edge of the device.

A device for associating a user emotion with electronic media is also described. The device may include a processor and memory in electronic communication with the processor. The device may further include instructions stored in the memory. The instructions may be executable by the processor to detect contact between a user of the device and a biopotential electrode array that is integrated with the device, acquire electrodermal data of the user via the biopotential electrode array, derive the user emotion based at least in part on the acquired electrodermal data, and associate the user emotion with the electronic media.

An apparatus for associating a user emotion with electronic media is also described. The apparatus may include means for detecting contact between a user of a device and a biopotential electrode array that is integrated with the device, means for acquiring electrodermal data of the user via the biopotential electrode array, means for deriving the user emotion based at least in part on the acquired electrodermal data, and means for associating the user emotion with the electronic media.

A computer program product for associating a user emotion with electronic media is also described. The computer program product may include a non-transitory computer-readable medium. The medium may store instructions executable by a processor to detect contact between a user of a device and a biopotential electrode array that is integrated with the device, acquire electrodermal data of the user via the biopotential electrode array, derive the user emotion based at least in part on the acquired electrodermal data, and associate the user emotion with the electronic media.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
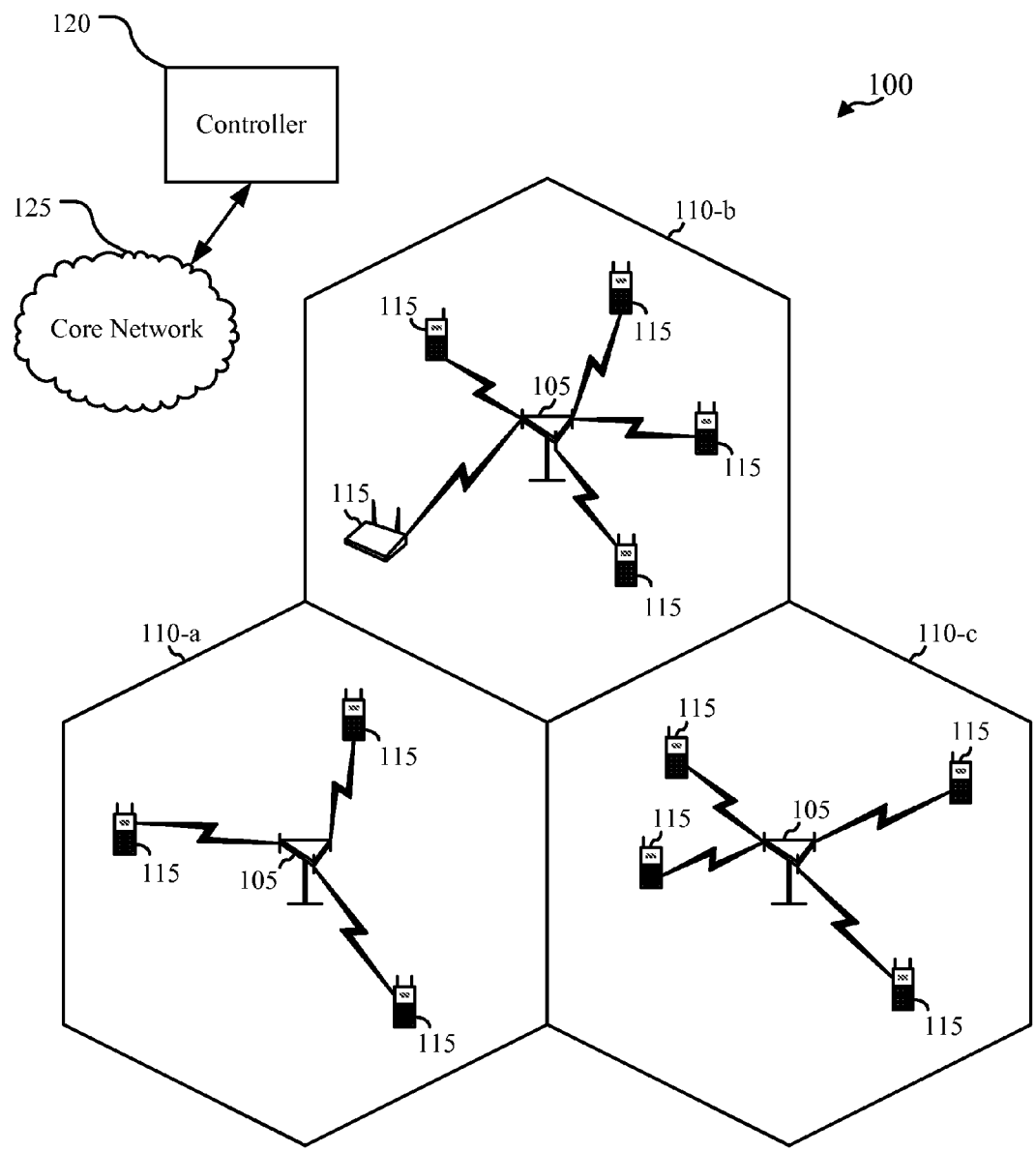
FIG. 1 is a block diagram of an example of a wireless communications system.

Systems, methods, devices, and apparatuses for associating a user emotion with electronic media are described.

There are a number of factors that may influence how a person feels about certain electronic media. For example, in digital photography, there are a number of elements that influence how a photographer feels about a photo. These factors may include emotions related to viewing the subject matter of the photo (e.g., "cute baby"; "I love these people"), emotions related to experiencing the environment in which the photo is taken (e.g., "this is a great vacation"; "got to snap the photo quick, before I fall off this ledge"), emotions related to the quality of the photo (e.g., "the lighting is just right"; "that one is too blurry"), or thoughts about how someone else is going to react when they see the photo (e.g., "I can't wait to show my friend"; "my friend is going to cry when they see this is true"). The emotions experienced by the photographer may include, for example, happiness, sadness, excitement, fear, pride, disappointment, etc. Often, the photographer's emotions are influenced by the personal traits of the photographer, such as the photographer's age, biases, or culture. Many of the same factors that influence how the photographer feels about a photo likewise influence how a subsequent viewer feels about the photo. The subsequent viewer may, however, experience an entirely different set of emotions and develop a different feeling about the photo. In fact, upon viewing the photo under a different set of conditions, even the photographer may experience different emotions and develop a different feeling about the photo.

With the advent of social networking, photos and other types of electronic media (e.g., digital videos) have become one of the major items that users share online. For some people, sorting through the numerous photos uploaded to a social networking site by their circle of friends, or deciding which of their photos to keep, is a daunting task for which they do not have time. Capturing the emotion that a photographer or viewer associates with a photo provides a basis for identifying photos that impacted the photographer or viewer most significantly, and for distilling a larger set of photos down to a more easily, viewable, manageable, or storable subset. Associating the photographer's or viewer's emotion with a digital photo also enables a subsequent viewer to compare their own emotion to the emotions of others.

A digital photo is one example of electronic media. Other types of electronic media include, for example, images (of which photos are a subset), videos, and audio recordings. Electronic media may be captured, presented, or played back on a mobile device such as a camera, mobile phone, tablet computer, mobile music player, mobile game controller, laptop computer, or on a stationary device such as a desktop computer, television or stationary display screen.

One or more emotions may be associated with electronic media for purposes other than social networking or file sorting. For example, an emotion may be associated with electronic media for the purpose of monitoring media quality, or for the purpose of determining what types of media, images or messages trigger a stronger emotional response in a person or persons. In the latter case, an emotion may be captured and associated with electronic media for the purpose of enabling an advertiser, newscaster or other media content provider to direct particular types of content to the viewer or listener.

In some embodiments, the emotion experienced by a user of a device may be associated with electronic media by: detecting contact between the user and a biopotential electrode array that is integrated with the device; acquiring electrodermal data of the user; deriving the user's emotion (i.e., "user emotion") based at least in part on the electrodermal data; and then associating the user emotion with the electronic media. The detection of contact between the user and the biopotential electrode array may occur, for example, during capture, presentation, or play back of the electronic media. The user emotion may be associated with the electronic media by saving the user emotion as metadata of the electronic media, or by saving the user emotion in a schema associated with the electronic media.

Electrodermal data for a user of a device may, in some cases, be acquired by a configurable biopotential electrode array. In one example, the array may be embedded on a surface area of a device, such as a surface of a handheld electronic communications device or other mobile device (e.g., a mobile phone or camera). The array may include a number of electrode tiles (or more broadly, a number of "electrodes"). The electrodes may include biosensors that collect electrodermal data of the device user. In one configuration, the electrodes (and their associated biosensors) may be activated to begin collecting the data when contact is detected between the electrodes and the skin of the user. The electrodes may be deactivated after contact between the electrodes and the skin of the user is terminated. A deactivated electrode may not collect the electrodermal data.

A contiguous area of a number of activated electrodes may function as a single electrode. The contiguous area may be referred to as an active electrode area (AEA). The electrodes within an AEA may collect electrodermal data of the user. The array may include one or more AEAs located at different positions along the array. For example, skin of the user may be in contact with a first group of electrodes (forming a first AEA) and a separate, second group of electrodes (forming a second AEA). The first AEA and the second AEA may not be adjacent to one another along the array. In addition, the first AEA and the second AEA may exist concurrently or noncurrently within the biopotential electrode array.

In one configuration, the electrodes of the array may be routinely polled to determine whether they are in contact with the skin of the user, or, if contact already exists, whether the contact between the skin of the user and the electrodes is maintained. The electrodermal data collected by the biosensors of the electrodes may be analyzed to determine an emotional state of the user.

The following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in orders different from those described, and various steps may be added, omitted, or combined. Also, features described with respect to certain embodiments may be combined in other embodiments.

The disclosed systems, methods and apparatus for associating a user emotion with electronic media can be applied to electronic media captured, presented, or played back by various types of devices. However, the techniques are particularly well-suited for application to electronic media that is captured, presented, or played back on or by mobile devices. Mobile devices include cellular phones and wireless communications devices, such as smart phones, but may also include personal digital assistants (PDAs), tablets, other handheld devices, netbooks, or notebook computers.

Techniques described herein may be used by mobile devices capable of communicating with various wireless communications systems, such as cellular wireless systems, Peer-to-Peer wireless communications, wireless local access networks (WLANs), ad hoc networks, satellite communications systems, and other systems. The terms "system" and "network" are often used interchangeably. These wireless communications systems may employ a variety of radio communication technologies for multiple access in a wireless system such as Code Division Multiple Access (CDMA), Time Division Multiple Access (TDMA), Frequency Division Multiple Access (FDMA), Orthogonal FDMA (OFDMA), Single-Carrier FDMA (SC-FDMA), and/or other technologies. Generally, wireless communications are conducted according to a standardized implementation of one or more radio communication technologies called a Radio Access Technology (RAT). A wireless communications system or network that implements a Radio Access Technology may be called a Radio Access Network (RAN).

Examples of Radio Access Technologies employing CDMA techniques include CDMA2000, Universal Terrestrial Radio Access (UTRA), etc. CDMA2000 covers IS-2000, IS-95, and IS-856 standards. IS-2000 Releases 0 and A are commonly referred to as CDMA2000 1x, 1x, etc. IS-856 (TIA-856) is commonly referred to as CDMA2000 1×EV-DO, High Rate Packet Data (HRPD), etc. UTRA includes Wideband CDMA (WCDMA) and other variants of CDMA. Examples of TDMA systems include various implementations of Global System for Mobile Communications (GSM). Examples of Radio Access Technologies employing FDMA and/or OFDMA include Ultra Mobile Broadband (UMB), Evolved UTRA (E-UTRA), IEEE 802.11 (Wi-Fi), IEEE 802.16 (WiMAX), IEEE 802.20, Flash-OFDM, etc. UTRA and E-UTRA are part of Universal Mobile Telecommunication System (UMTS). 3GPP Long Term Evolution (LTE) and LTE-Advanced (LTE-A) are new releases of UMTS that use E-UTRA. UTRA, E-UTRA, UMTS, LTE, LTE-A, and GSM are described in documents from an organization named "3rd Generation Partnership Project" (3GPP). CDMA2000 and UMB are described in documents from an organization named "3rd Generation Partnership Project 2" (3GPP2). The techniques described herein may be used on devices that use the systems and radio technologies mentioned above as well as other systems and radio technologies.

Referring first to FIG. 1, a block diagram illustrates an example of a wireless communications system 100. The system 100 includes base stations 105 (or cells), mobile devices 115, a base station controller 120, and a core network 125 (the controller 120 may be integrated into the core network 125). The system 100 may support operation on multiple carriers (waveform signals of different frequencies).

The base stations 105 may wirelessly communicate with the mobile devices 115 via a base station antenna (not shown). The base stations 105 may communicate with the mobile devices 115 under the control of the base station controller 120 via multiple carriers. Each of the base station 105 sites may provide communication coverage for a respective geographic area. The coverage area for each base station 105 here is identified as 110-a, 110-b, or 110-c. The coverage area for a base station may be divided into sectors (not shown, but making up only a portion of the coverage area). The system 100 may include base stations 105 of different types (e.g., macro, micro, and/or pico base stations). There may be overlapping coverage areas for different technologies.

The mobile devices 115 may be dispersed throughout the coverage areas 110. The mobile devices 115 may be alternately referred to as mobile stations, access terminals (ATs), user equipments (UEs), subscriber stations (SSs), or subscriber units. The mobile devices 115 may include cellular phones and wireless communications devices, but may also include personal digital assistants (PDAs), other handheld devices, netbooks, notebook computers, etc.

The base stations 105 may allow users of the mobile devices 115 to communicate with each other. For example, a mobile device 115 may send electronic communications (e.g., email, text messages, voicemail messages, images, videos, audio recordings, etc.) to another mobile device. Users of different mobile devices 115 may also engage in real-time conversations (i.e., phone calls), web browsing, media capture, and data sharing using their respective devices. Some of the activities in which the mobile devices 115 engage (e.g., web browsing) may require electronic communications with servers reachable via the core network.

Some of the data captured, received, retrieved or transmitted by the mobile devices 115 may take the form of electronic media such as images, videos, audio recordings, or web pages. When the electronic media is captured, presented or played back on one of the mobile devices 115, the mobile device may execute one or more processes to associate user emotion with the electronic media. The electronic media and its associated user emotion may then be transmitted to another of the mobile devices 115, or to a server, where the user emotion may be used or viewed for a variety of purposes, including those purposes already described.

Figure 2:
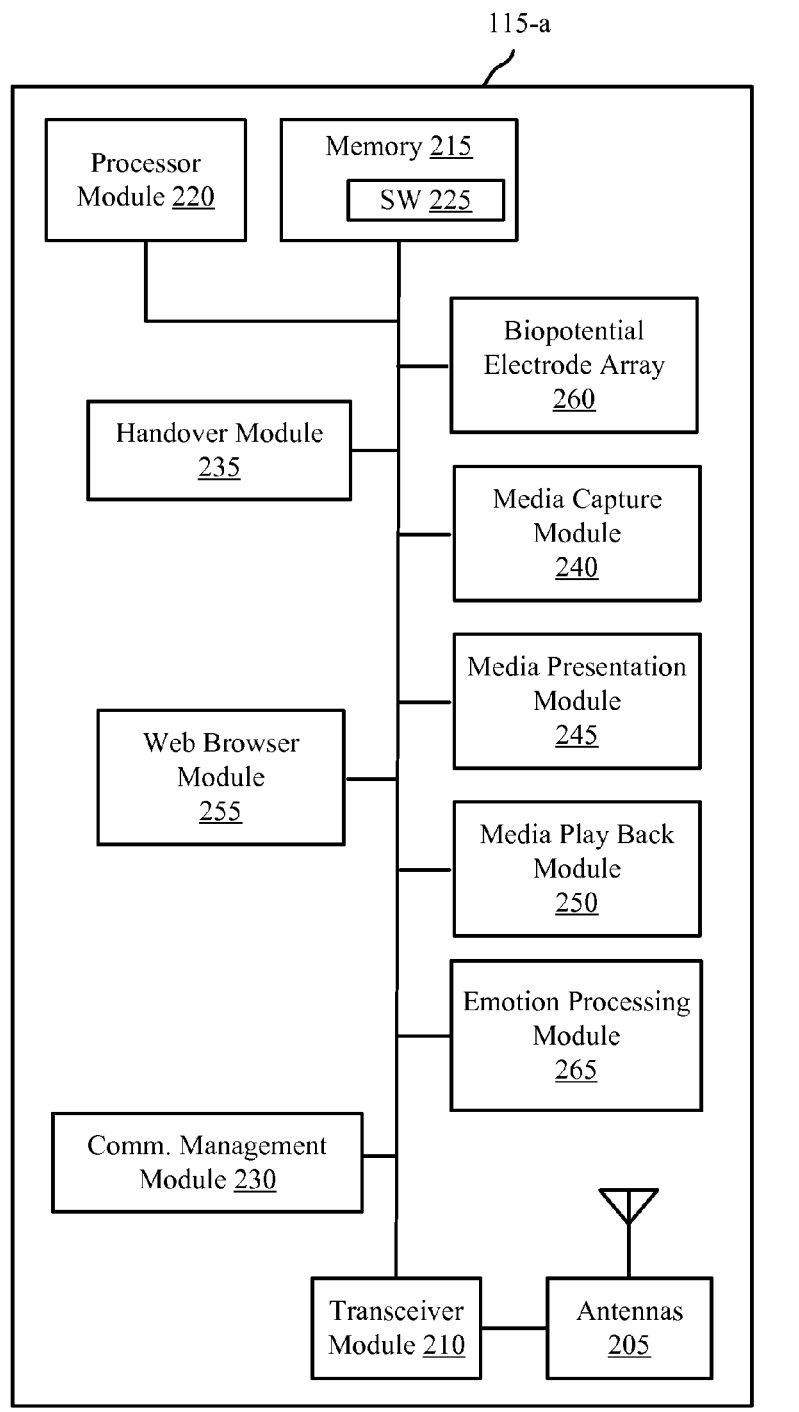
FIG. 2 is a block diagram of a first example of a mobile device that associates user emotion with electronic media in accordance with various embodiments.

Turning now to FIG. 2, a block diagram 200 illustrates a mobile device 115-a for associating user emotion with electronic media in accordance with various embodiments. The mobile device 115-a may have any of various configurations, such as personal computers (e.g., laptop computers, netbook computers, tablet computers, etc.), mobile or cellular telephones, PDAs, digital video recorders (DVRs), internet appliances, gaming consoles, e-readers, etc. The mobile device 115-a may have an internal power supply, such as a small battery, to facilitate mobile operation. In some embodiments, the mobile device 115-a may be an example of the mobile device 115 of FIG. 1. The mobile device 115-a may be a multi-mode mobile device.

The mobile device 115-a may include antennas 205, a transceiver module 210, memory 215, and a processor module 220, which each may be in communication, directly or indirectly, with each other (e.g., via one or more buses). The transceiver module 210 is configured to communicate bi-directionally, via the antennas 205 and/or one or more wired or wireless links, with one or more networks, as described above. For example, the transceiver module 210 may be configured to communicate bi-directionally with base stations 105 of FIG. 1. The transceiver module 210 may include a modem configured to modulate the packets and provide the modulated packets to the antennas 205 for transmission, and to demodulate packets received from the antennas 205. While the mobile device 115-a may include a single antenna, the mobile device 115-a will typically include multiple antennas 205 for multiple links.

The memory 215 may include random access memory (RAM) and read-only memory (ROM). The memory 215 may store computer-readable, computer-executable software code 225 containing instructions that are configured to, when executed, cause the processor module 220 to perform various functions. Alternatively, the software code 225 may not be directly executable by the processor module 220 but be configured to cause the computer (e.g., when compiled and executed) to perform functions described herein.

The processor module 220 may include an intelligent hardware device, e.g., a central processing unit (CPU) such as those made by Intel® Corporation or AMD®, a microcontroller, an application-specific integrated circuit (ASIC), etc. The processor module 220 may include a speech encoder (not shown) configured to receive audio via a microphone, convert the audio into packets (e.g., 30 ms in length) representative of the received audio, provide the audio packets to the transceiver module 210, and provide indications of whether a user is speaking. Alternatively, an encoder may only provide packets to the transceiver module 210, with the provision or withholding/suppression of the packet itself providing the indication of whether a user is speaking.

According to the architecture of FIG. 2, the mobile device 115-a may further include a communications management module 230. The communications management module 230 may manage communications with other mobile devices 115. By way of example, the communications management module 230 may be a component of the mobile device 115-a in communication with some or all of the other components of the mobile device 115-a via a bus. Alternatively, functionality of the communications management module 230 may be implemented as a component of the transceiver module 210, as a computer program product (e.g., software), and/or as one or more controller elements of the processor module 220.

In some embodiments, a handover module 235 may be utilized to perform reselection and handover procedures of the mobile device 115-a from one base station 105 to another. For example, the handover module 235 may perform a handover procedure of the mobile device 115-a from signaling carrier to another signaling carrier, a traffic carrier to another traffic carrier and between a signaling and traffic carrier.

The device 115-a may include one or more of a media capture module 240, a media presentation module 245, a media play back module 250, or a web browser module 255. These modules may be components of the mobile device 115-a in communication with some or all of the other components of the mobile device 115-a via a bus. Alternatively, functionality of any or all of these modules may be implemented as a component of the transceiver module 210, as a computer program product, and/or as one or more controller elements of the processor module 220.

The media capture module 240 may be configured, for example, to capture an image, video, or audio recording using a camera and/or microphone on-board, or in communication with, the mobile device 115-a. The media presentation module 245 may be configured, for example, to present images, videos, or web pages on a screen of the mobile device 115-a (or a screen connected thereto). The media play back module 250 may be configured, for example, to play audio recordings or videos on the mobile device 115-a (or via speakers and/or a screen attached thereto). The web browser module 255 may be configured, for example, to present or play back various types of electronic media embedded within (or linked to) a web page. In some cases, the electronic media presented or played back via the media presentation module 245, media play back module 250, or web browser module 255 may be presented or played back, upon capture, via the media capture module 240 or transceiver module 210. In other cases, the electronic media played back via the media presentation module 245, media play back module 250, or web browser module 255 may be presented or played back upon retrieval from the memory 215 or other physical data storage (including, for example, external data storage connected to the mobile device 115-a).

In some embodiments, the device 115-a may include a biopotential electrode array 260. The array 260 may acquire electrodermal data of a user of the device 115-a. In some cases, the biopotential electrode array may be or include a configurable biopotential array of electrodes or electrode tiles. The electrodes may be arranged in the array in different configurations and with different shapes. The array may be embedded along a surface area of the device 115-a. Biosensors may be incorporated with the electrodes to collect electrodermal data associated with the user of the device 115-a. Electrodes that are in contact with the skin of the user may be activated to begin collecting the data. For example, as the user holds the mobile device 115-a in his/her hand, the electrodes in contact with the skin of the user's hand, fingers, etc. may be activated. Activated electrodes may be deactivated after contact with the user's skin has terminated. For example, as the user changes the position of his/her grip of the device 115, the electrodes that are currently activated may be deactivated, and the electrodes that are currently deactivated may be activated.

An emotion processing module 265 may communicate with various ones of the media capture module 240, media presentation module 245, media play back module 250, web browser module 255, and biopotential electrode array 260, as well as other components and modules on-board or external to the mobile device 115-a. The emotion processing module 265 may associate user emotion (e.g., the emotion of the user holding the mobile device 115-a) with electronic media captured, presented, or played back by the mobile device 115-a. The emotion processing module 265 may be a component of the mobile device 115-a in communication with some or all of the other components of the mobile device 115-a via a bus. Alternatively, functionality of the emotion processing module 265 may be implemented as a component of the transceiver module 210, as a computer program product, and/or as one or more controller elements of the processor module 220.

Figure 3:
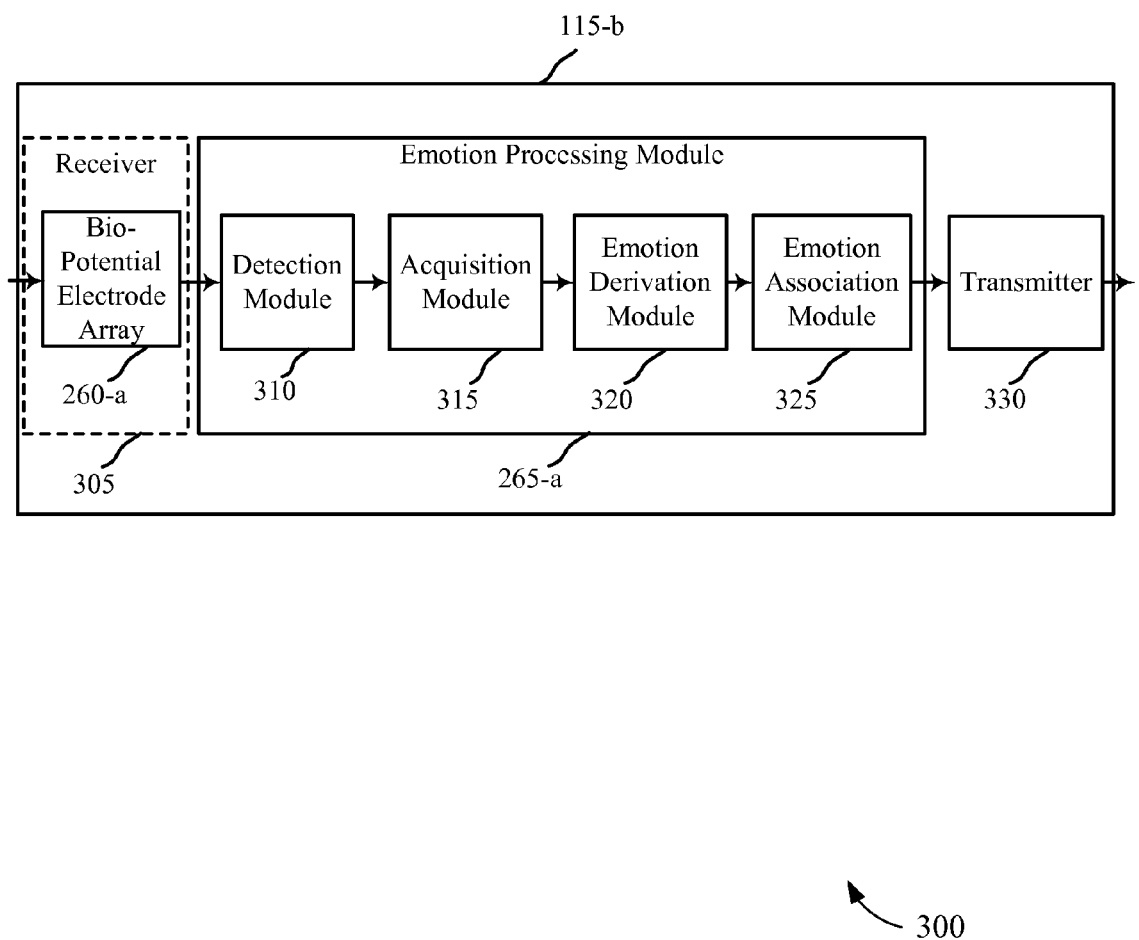
FIG. 3 is a block diagram of a second example of a mobile device that associates user emotion with electronic media in accordance with various embodiments.

FIG. 3 is a block diagram 300 illustrating another example of a mobile device. The mobile device 115-b may be an example of the mobile device 115 of FIGS. 1 and/or 2. In one embodiment, the mobile device 115-b may include a biopotential electrode array 260-a, an emotion processing module 265-a, and a transmitter 330. The biopotential electrode array 260-a may be an example of the biopotential electrode array 260 of FIG. 2, and may generate signals relating to contact between the skin of the user of the device 115-b and a surface area of the device 115-a. The biopotential electrode array 260-a may be one element of a receiver 305, which receiver 305 may include a wireless receiver for receiving signals and electronic communications from other devices, such as the base stations 105 or other mobile devices 115. The receiver 305 may also include a wired receiver and may receive signals and electronic communications via a cable (e.g., from one or more accessories). The transmitter 330 may include a wireless transmitter and transmit signals and electronic communications to other devices, such as the base stations 105 or other mobile devices 115. The transmitter 330 may also include a wired transmitter.

The emotion processing module 265-a may be an example of the emotion processing module 265 of FIG. 2. The emotion processing module 265-a may include a detection module 310, an acquisition module 315, an emotion derivation module 320, and an emotion association module 325. In one example, the detection module 310 may analyze signals relating to contact between a user of the device 115-b and a biopotential electrode array integrated on one or more surfaces of the device 115-b, to determine whether sufficient contact exists between the user's skin and the biopotential electrode array 260-a. In some embodiments, this may include determining whether contact exists between the user's skin and at least two or more electrode tiles of the biopotential electrode array 260-a.

The acquisition module 315 may acquire electrodermal data of the user of the device 115-b via the biopotential electrode array 260-a. The output of the acquisition module 315 may be, for example, a skin conductance response (SCR). An SCR is indicative of the conductance of a subject's eccrine sweat glands, and may provide useful electrodermal data about the subject, such as the subject's state of arousal. A subject may become aroused, for example, as a result of experiencing emotions such as attraction, excitement, or fear. The emotion derivation module 320 may process the SCR or other output of the acquisition module 315 to derive such user emotion. The emotion association module 325 may associate the user emotion with the electronic media for which the user emotion was derived.

Figure 4:
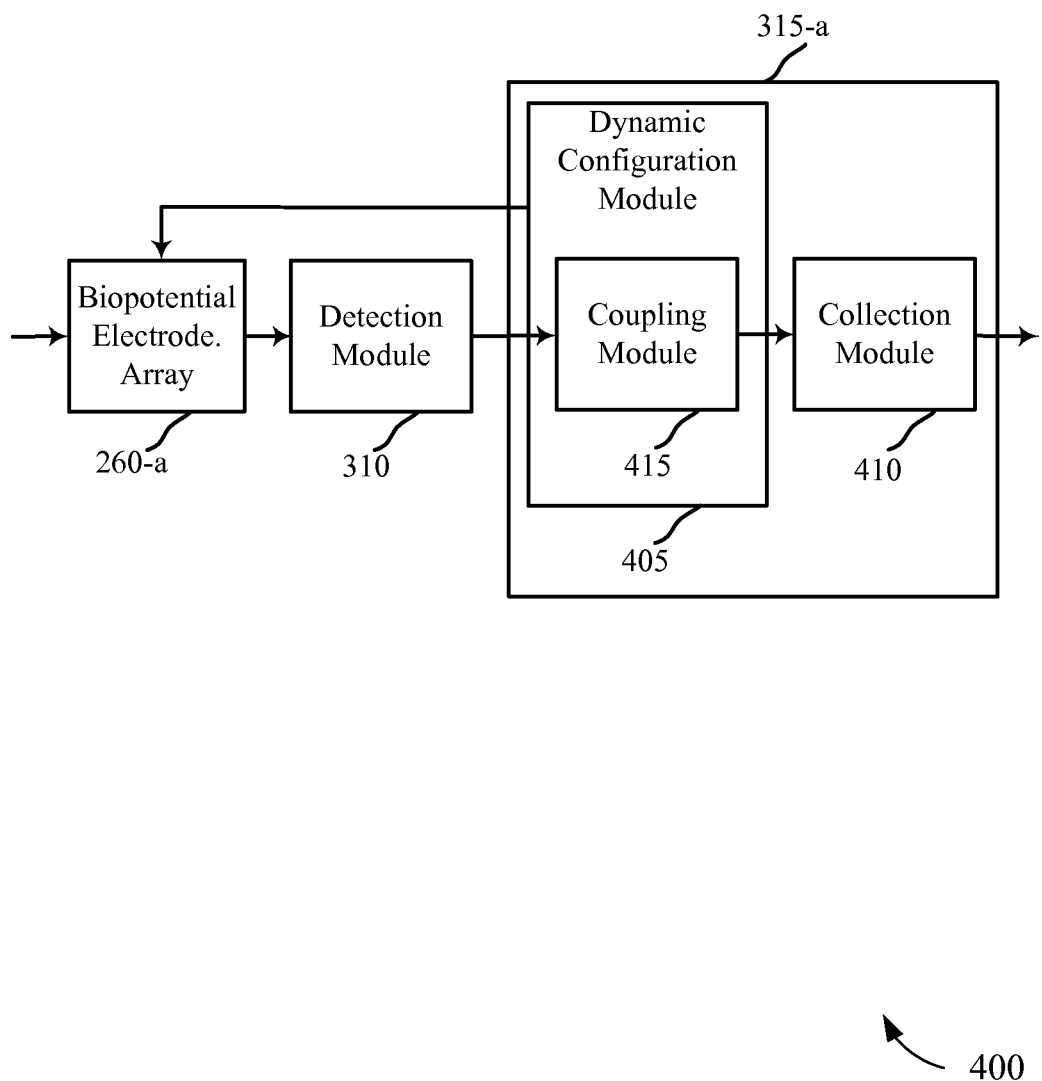
FIG. 4 is a block diagram of a first example of an acquisition module for acquiring electrodermal data, in communication with a biopotential electrode array.

FIG. 4 is a block diagram 400 illustrating a first example of an acquisition module 315-a, in communication with the biopotential electrode array 260-a and detection module 310. The acquisition module 315-a may be an example of the acquisition module 315 of FIG. 3. The acquisition module 315-a may include a dynamic configuration module 405 and a collection module 410.

The dynamic configuration module 405 may comprise a coupling module 415. The coupling module 415 may couple together the electrodes of the biopotential electrode array 260-a that are detected to be in contact with the user's skin. For example, each electrode may be connected to adjacent electrodes with respective electronic switches. An example of the switch may include a field effect transistor (FET). When a particular electrode tile and at least one adjacent electrode tile come in contact with the skin, the electronic switch between these two electrodes may be closed due to electrical conductive properties of the skin, thus creating a closed circuit between the electrodes. A closed circuit may activate the electrodes. The electronic switch between electrodes that are not in contact with the skin may not be closed, leaving an open circuit. These may be referred to as inactive electrodes.

The collection module 410 may collect data gathered from the activated electrodes. For example, the module 410 may collect electrodermal data associated with the user (also referred to as "electrodermal data" of the user). This data may be gathered via biosensors incorporated with the electrode tiles. As a result, electrodes that are active may collect the data, while inactive electrodes may not participate in gathering the electrodermal data of the user. The configurable biopotential electrode array architecture described herein may minimize electrical noise since electrodes that are inactive (not in contact with the user's skin) are not actively collecting data.

Figure 5:
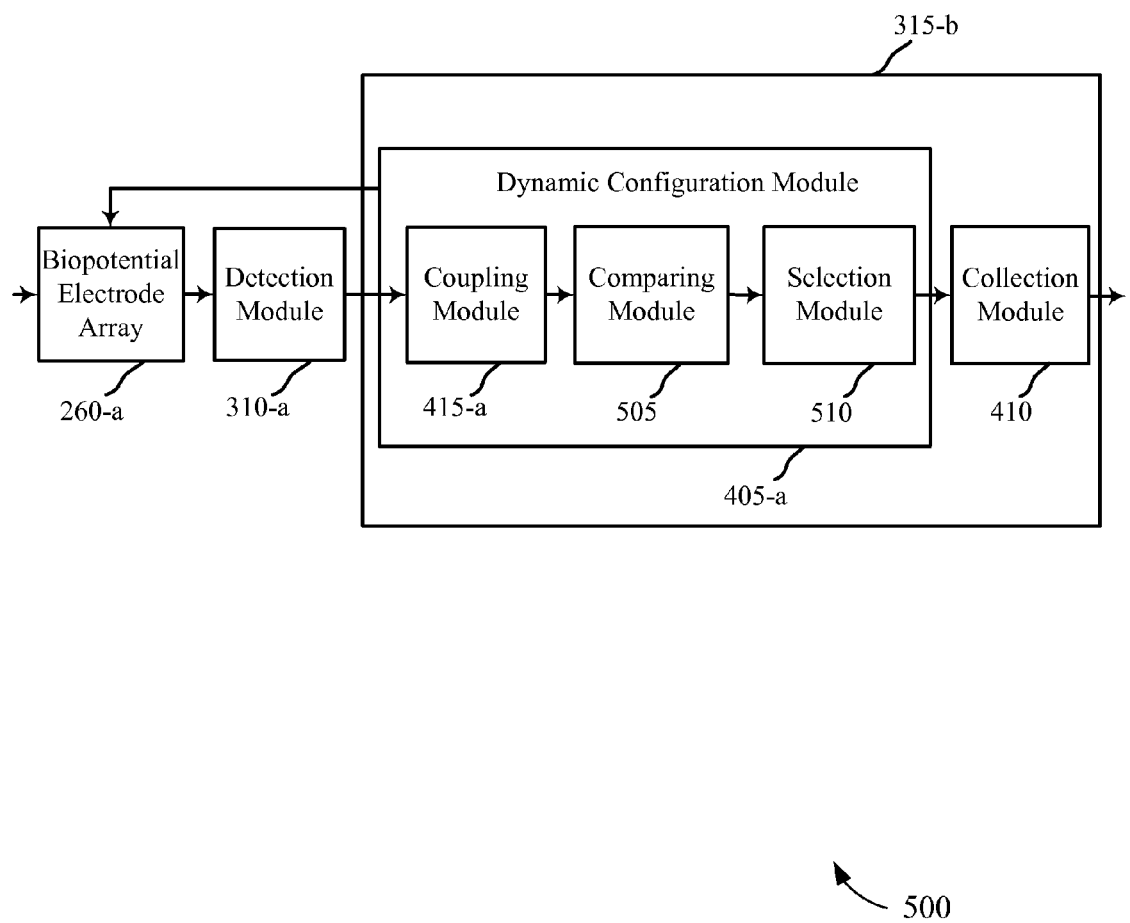
FIG. 5 is a block diagram of a second example of an acquisition module for acquiring electrodermal data, in communication with a biopotential electrode array.

Referring now to FIG. 5, a block diagram 500 illustrates a second example of an acquisition module 315-b, in communication with the biopotential electrode array 260-a and a detection module 310-a. The acquisition module 315-b may be an example of the acquisition module 315 of FIGS. 3 and/or 4. The acquisition module 315-b may include a dynamic configuration module 405-a and the collection module 410 (previously described). The dynamic configuration module 405-a may include a coupling module 415-a, a comparing module 505 and a selection module 510. The detection module 310-a may detect contact between a first group of electrode tiles embedded on an external portion of the device 115-b and the skin of a user of the device 115-b. The coupling module 415-a may electrically couple the first group of electrode tiles based on the detection module 310-a detecting contact. In one configuration, the first group of coupled electrode tiles may form a first active electrode area (AEA). In one example, the detection module 310-a may detect contact between the user's skin and a second group of electrode tiles. The coupling module 415-a may also electrically couple the second group of electrodes to form a second AEA. Each of the electrodes in the first AEA and the second AEA may include a biosensor that may begin collect data regarding the user of the device 115-b. In one example, the number of AEA may exceed a minimum number of AEAs needed to collect the data. The comparing module 505 may compare a signal quality metric associated with each AEA. For example, the comparing module 505 may compare the quality of the electrical signal detected from the skin of the user at each AEA. The selection module 510 may select which AEAs to receive data from based on the comparison of the signal quality metrics of each AEA. Examples of the signal quality metric may include, but are not limited to, a signal-to-noise ratio (SNR).

Figure 6:
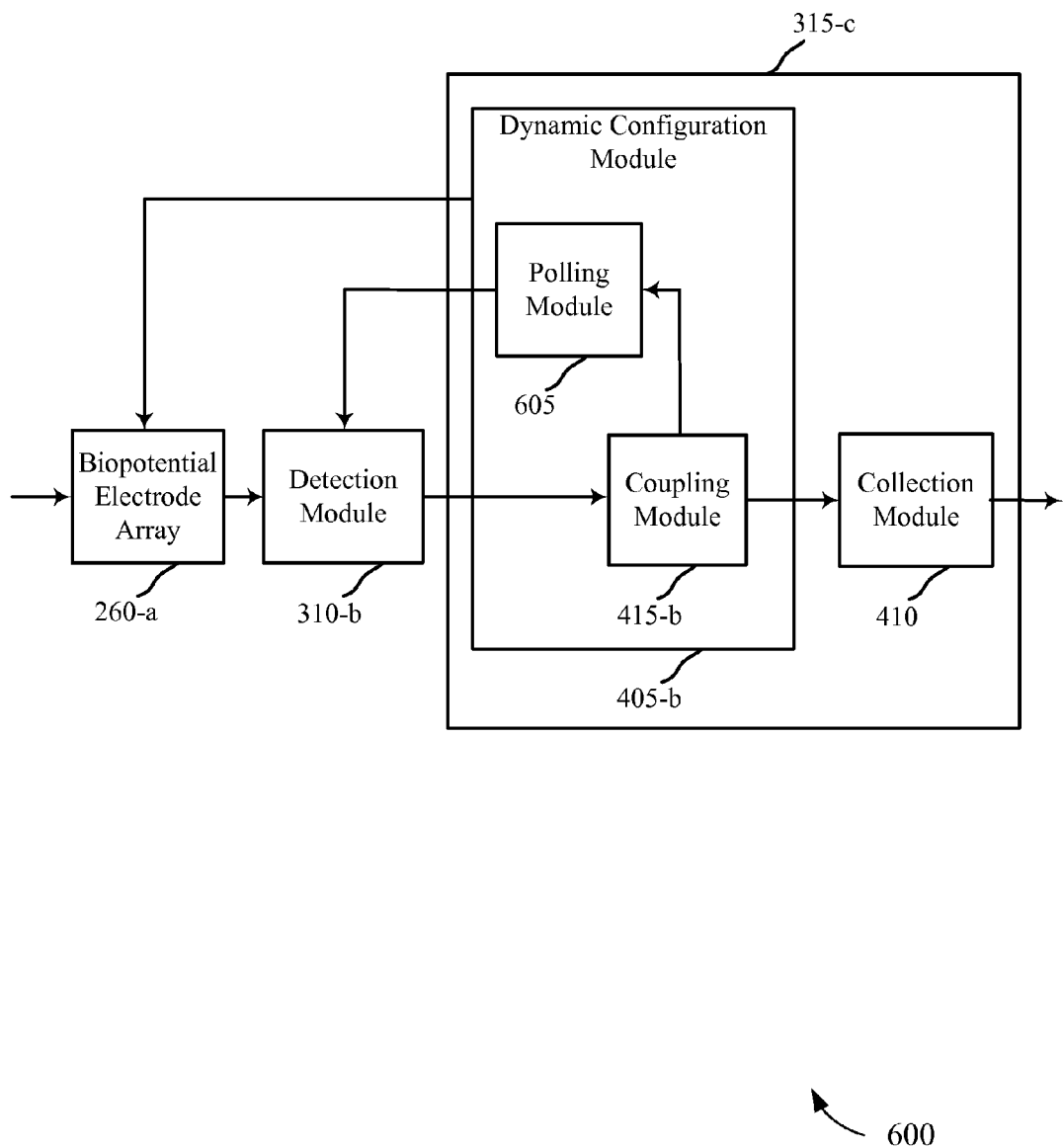
FIG. 6 is a block diagram of a third example of an acquisition module for acquiring electrodermal data, in communication with a biopotential electrode array.

FIG. 6 is a block diagram 600 illustrating a third example of an acquisition module 315-c, in communication with the biopotential electrode array 260-*a* and a detection module 310-*b*. The acquisition module 315-*c* may be an example of the acquisition module 315 of FIGS. 3, 4, and/or 5. The acquisition module 315-*c* may include a dynamic configuration module 405-*b* and the collection module 410 (previously described). The dynamic configuration module 405-*b* may further include a coupling module 415-*b* and a polling module 605. In one example, the coupling module 415-*b* may electrically couple electrode tiles when the detection module 310-*b* detects contact between the electrodes and skin of a user.

In one configuration, the polling module 605 may routinely poll the coupled electrodes to determine whether the contact with the use's skin is maintained. An example of the polling module 605 may be a galvanic skin response (GSR) sensor. When skin contacts the electrodes, the current between the contacted electrodes may be greater than zero, due to the conductive properties of the skin. As a result, the polling module 605 may poll the flow of current between adjacent electrodes. If the flow of current between two polled electrodes is zero, the detection module 310-*b* may detect that the contact with the use's skin no longer exists. The coupling module 415-*b* may decouple the electrodes after the contact with the user's skin is terminated. The polling module 605 may also poll the flow of current between previously uncoupled electrodes to determine whether contact with the user's skin may exist. If the flow of current is greater than zero between at least two adjacent electrodes, the detection module 310-*b* may detect contact between these previously uncoupled electrodes and the skin of the user. The coupling module 415-*b* may then electrically couple these electrodes. While coupled, electrodes remain in contact with the user's skin, and the collection module 415-*b* may collect electrodermal data of the user via biosensors associated with the electrodes.

Figure 7:
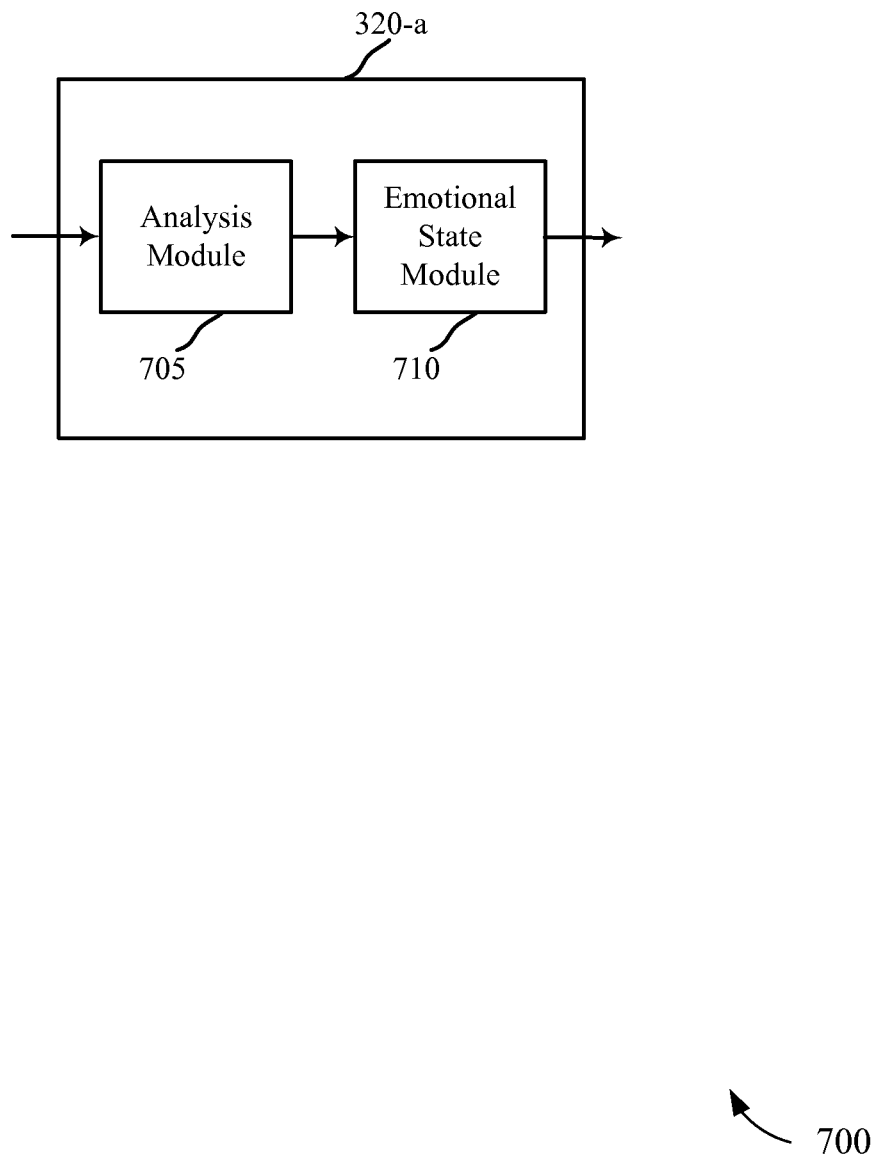
FIG. 7 is a block diagram of an example of an emotion derivation module.

FIG. 7 is a block diagram 700 illustrating an example of an emotion derivation module 320-*a*. The emotion derivation module 320-*a* may be an example of the emotion derivation module 320 of FIG. 3. The emotion derivation module 320-*a* may include an analysis module 705 and an emotional state module 710. The analysis module 705 may analyze the collected electrodermal data (e.g., SCR) of the user. In one configuration, the emotional state module 710 may correlate the electrodermal data with an emotional state of the user (e.g., happy, excited, sad, angry, anxious, stressed) based on the analysis. In one example, the emotional state module 710 may access a database that stores various emotional states and a corresponding SCR for one or more emotional states. The database may be stored locally on a device 115 or remotely on a server or some other computing device.

Figure 8:
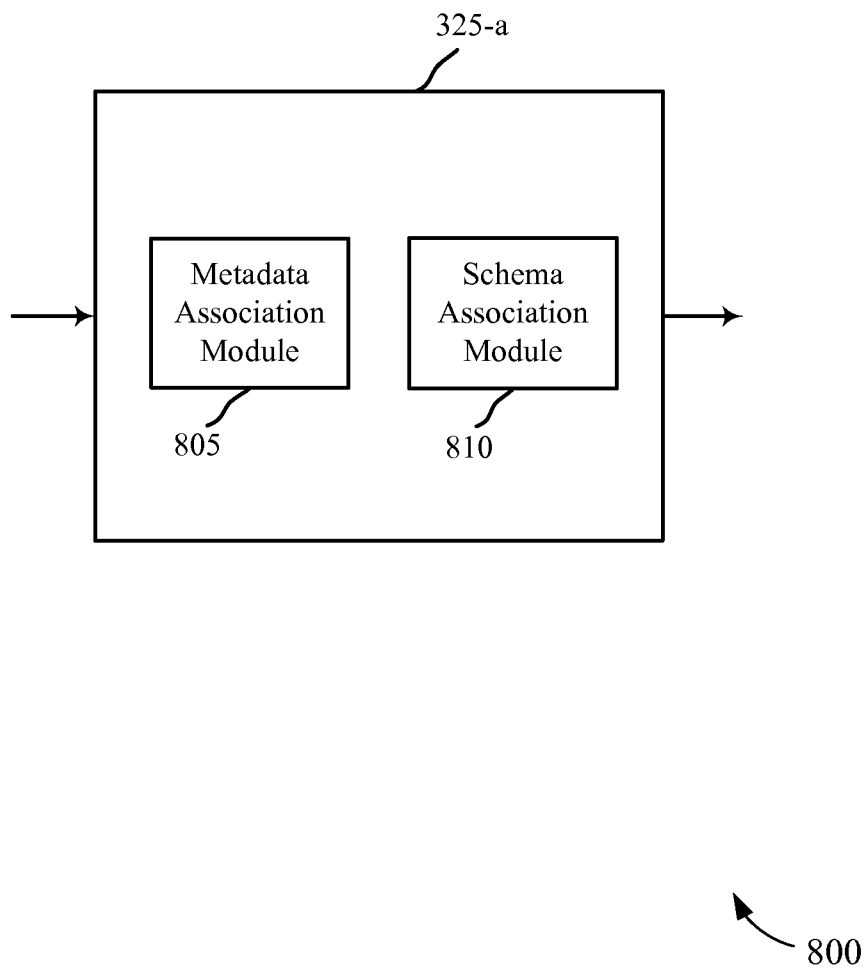
FIG. 8 is a block diagram of an example of an emotion association module.

Referring now to FIG. 8, a block diagram 800 illustrates one example of an emotion association module 325-*a*. In one configuration, the emotion association module 325-*a* may be an example of the emotion association module 325 of FIG. 3. The emotion association module 325-*a* may include, for example, one or more of a metadata association module 805 and a schema association module 810. The metadata association module 805 may associate a user emotion with electronic media by storing the user emotion in the associated metadata of the electronic media. For example, in the case of a Joint Photographic Experts Group (JPEG) image, the metadata association module 805 may store an indicator of the user emotion (or "tag") in an Exchangeable Image File Format (EXIF) tag of the JPEG image.

The schema association module 810 may associate a user emotion with electronic media by storing the user emotion in a schema associated with the electronic media. For example, the schema association module 810 may store an indicator of the user emotion in a custom eXtensible Metadata Platform (XMP) schema. The indicator (or "tag") may be created using the World Wide Web Consortium (W3C) Emotion Markup Language (EML). The form of such an EML tag might be:

```
<emotion>
    <category name="Disgust" />
    <intensity value="0.82"/>
/emotion>
<emotion>
    <category name="Contempt"/>
    <intensity value="0.35"/>
/emotion>
<emotion>
    <category name="Anger"/>
    <intensity value="0.12"/>
/emotion>
<emotion>
    <category name="Surprise"/>
    <intensity value="0.53"/>
/emotion>
```

In some embodiments, the emotion association module 325-*a* may first invoke the metadata association module 805. If the metadata association module 805 is unable to store an indicator of user emotion in the metadata of the electronic media, the emotion association module 325-*a* may invoke the schema association module 810. In other embodiments, the emotion association module 325-*a* may invoke the metadata association module 805 or schema association module 810 based on an electronic media type (e.g., image, video or audio) or electronic media file type (e.g., JPEG or Tagged Image File Format (TIFF)).

Figure 9:
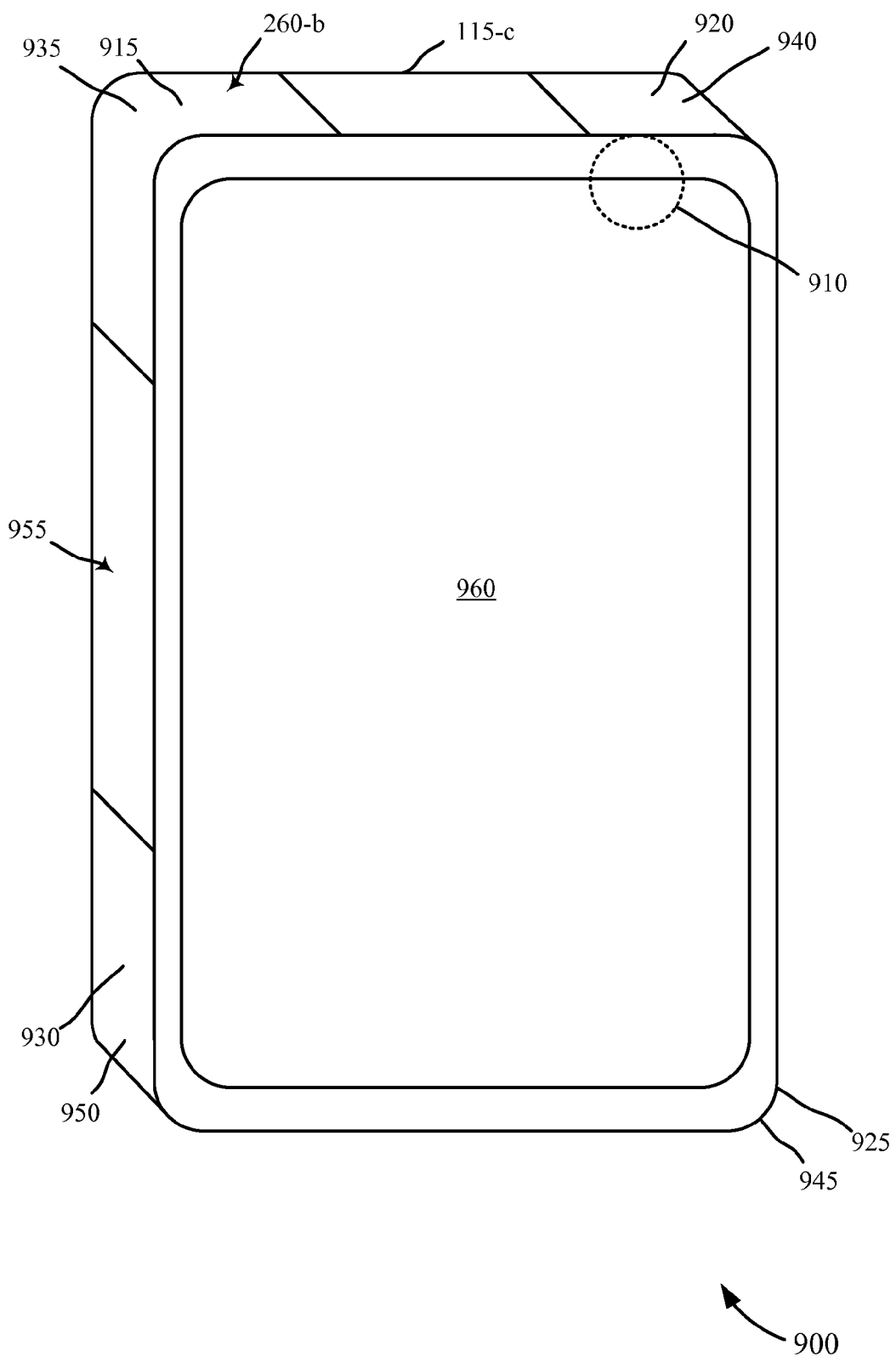
FIG. 9 is a block diagram of a third example of a mobile device that associates user emotion with electronic media in accordance with various embodiments.

FIG. 9 illustrates a block diagram 900 of one example of a mobile device 115-*c* having a biopotential electrode array 260-*b* embedded on a surface area of the mobile device 115-*c*. The array 260-*b* may be an example of the biopotential electrode array of FIGS. 1, 2, 3, 4, 5, and/or 6. In one configuration, the mobile device 115-*c* may be an example of the mobile device 115 of FIGS. 1, 2, and/or 3. The device 115-*c* may include a number of surface areas, such as a side edge surface area 955 (or simply "side edge"), a display surface area 960, and a surface area opposite the display surface area (e.g., a surface area on which an aperture 910 of a camera may be located). The array 260-*b* may be embedded or positioned on the side edge 955 in this example, and more particularly may be distributed amongst regions 915, 920, 925 and 930 located at the four corners 935, 940, 945 and 950 of the device 115-*c*. It is to be understood, however, that the array 260-*b* may be embedded or positioned on other surface areas of the mobile device 115-*c*.

Figure 10:
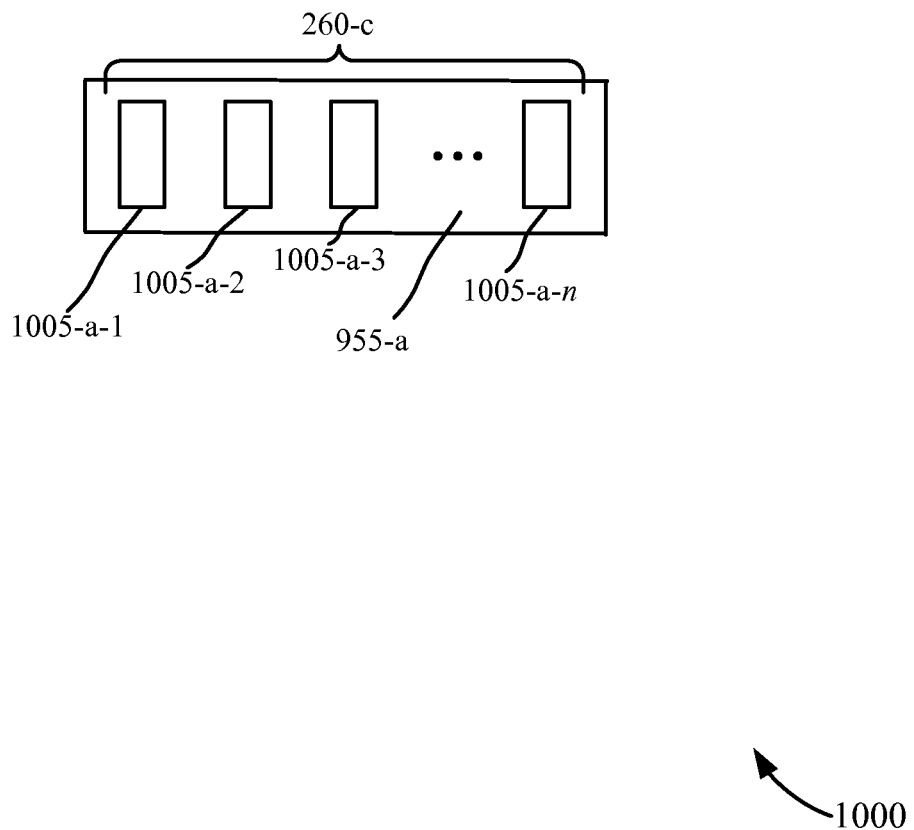
FIG. 10 is a block diagram of a first example of a biopotential electrode array.

Referring now to FIG. 10, a block diagram 1000 illustrates one example of a biopotential electrode array 260-*c*. In one configuration, the biopotential electrode array 260-*c* may be an example of the biopotential electrode array 260 of FIGS. 1, 2, 3, 4, 5, 6, and/or 9. The biopotential electrode array 260-*c* may include a number of electrode tiles 1005-*a*-1, 1005-*a*-2, 1005-*a*-3, and 1005-*a*-*n* on one or more surfaces 955-*a* of a device. In some embodiments, the electrode tiles may be formed of stainless steel. Each electrode tile 1005 may include a biosensor. Examples of biosensors may include galvanic skin response (GSR) sensors and other biopotential sensors. As illustrated, the electrode tiles 1005 may be rectangular in shape. Spaces may exist between adjacent ones of the electrode tiles. Larger spaces may exist between some of the electrode tiles, because the electrode tiles 1005 may be distributed over different regions of a device, such as the regions 915, 920, 925, 930 of the device 115-c shown in FIG. 9. When current is detected flowing between adjacent electrodes due to contact with human skin, an electronic switch between the electrodes may be closed to create a closed circuit. The closed circuit may allow the electrodes to collect electrodermal data, while electrodes that are in an open circuit state (are not in contact with human skin) may not participate in collecting the data.

Figure 11:
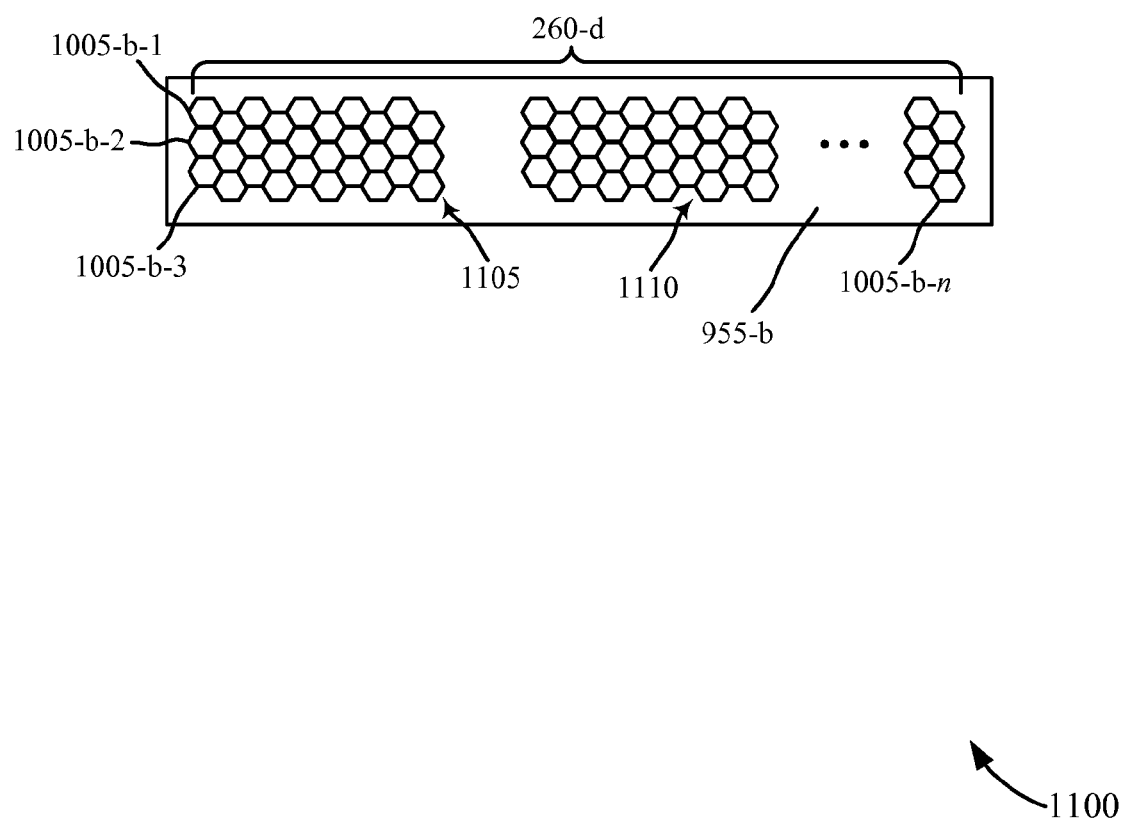
FIG. 11 is a block diagram of a second example of a biopotential electrode array.

FIG. 11 is a block diagram 1100 illustrating another example of a biopotential electrode array 260-d that includes electrode tiles 1005-b-1-1005-b-n embedded on a surface area 955-b of a device. The biopotential electrode array 260-d may be an example of the biopotential electrode array 260 of FIGS. 1, 2, 3, 4, 5, 6, 9, and/or 10. The electrode tiles 1005 may be hexagonal in shape. As illustrated, very little space may exist between the adjacent electrode tiles in a group of electrode tiles 1105 or 1110. However, larger spaces may exist between different groups of electrode tiles 1105, 1110, as may be required when groups of electrode tiles are distributed amongst different regions of a device (e.g., amongst the regions 915, 920, 925, 930 of the device 115-c shown in FIG. 9). Each electrode tile may include a biosensor to collect information about a device user. The biosensors may begin to collect the data when their respective electrodes are in contact with the skin of a user.

Figure 12:
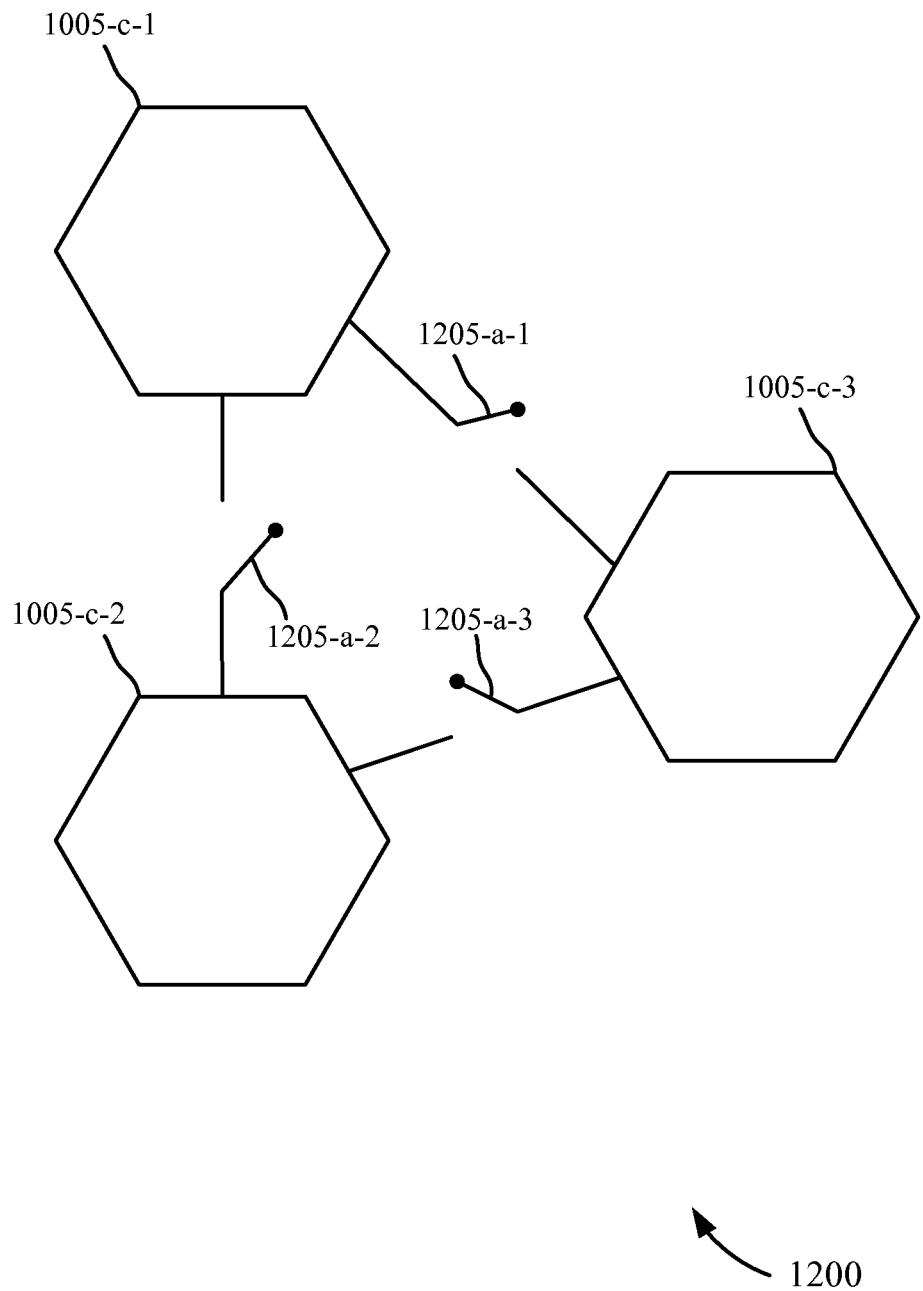
FIG. 12 is a block diagram of an example collection of electrodes tiles of a biopotential array.

Referring now to FIG. 12, a collection 1200 of electrode tiles 1005-c-1, 1005-c-2, 1005-c-3 is illustrated. The electrode tiles may be examples of the electrode tiles 1005 of FIGS. 10 and/or 11. In one example, an electronic switch 1205-a-1, 1205-a-2, or 1205-a-3 may exist between adjacent electrode tiles. When the skin of a user contacts at least two adjacent electrode tiles, the electronic switch between the at least two electrodes may be closed due to the flow of current between the at least two adjacent electrode tiles. The biosensors associated with the at least two electrode tiles may begin to collect electrodermal data associated with the user. For example, the user may touch a first electrode tile 1005-c-1 and a second electrode tile 1005-c-2. When contact with the user's skin is detected, the electrodes may be electrically coupled by closing the electronic switch 1205-a-2 between them. With the switch closed, the biosensors associated with the first and second electrode tiles 1005-c-1, 1005-c-2 may collect data about the user. The switch 1205-a-2 may be opened (and the electrodes uncoupled) when contact between the electrode tiles and the user is terminated.

Figure 13:
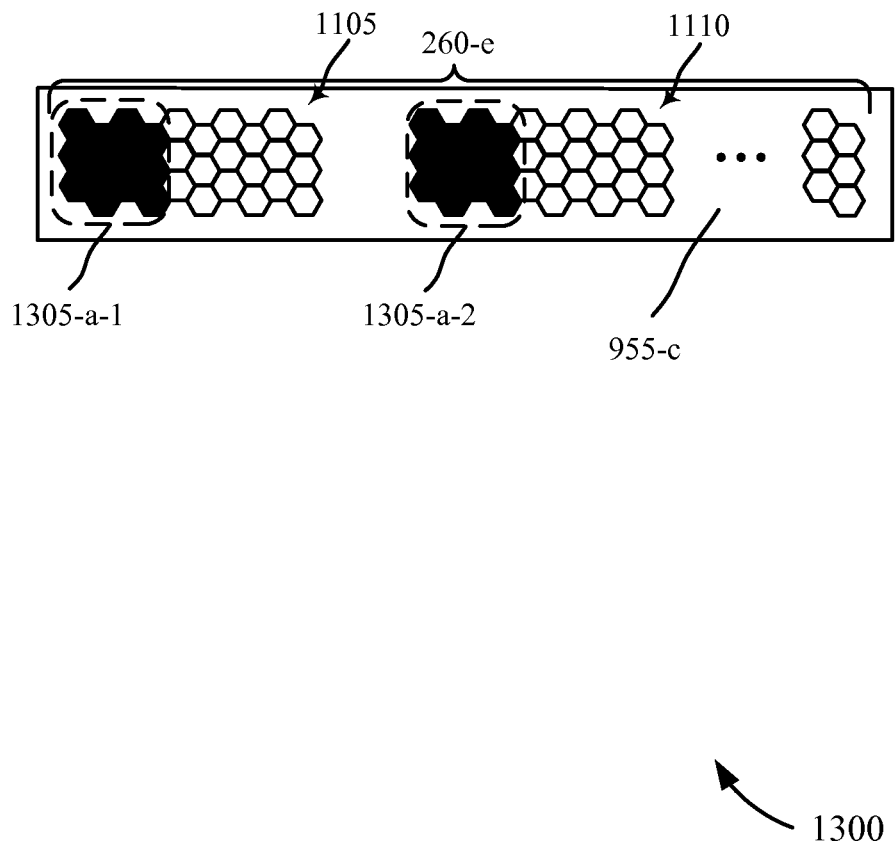
FIG. 13 is a block diagram showing an operating state of a biopotential electrode array.

FIG. 13 is a block diagram 1300 illustrating an operational state of a biopotential electrode array 260-e. The array 260-e may be an example of the biopotential electrode array of FIGS. 1, 2, 3, 4, 5, 6, 9, 10, and/or 11. The array 260-e may include a number of AEAs 1305-a-1, 1305-a-2 created by user contact with the biopotential electrode array 260-e. In accord with one example of user contact with the biopotential electrode array 260-e, the array 260-e may be configured to include a first AEA 1305-a-1 and a second AEA 1305-a-2. Each AEA may include at least two electrode tiles that have been electrically coupled. In other words, each AEA may include electrode tiles that are in contact with the skin of a user. As the user's grip of a device shifts, the position of one or both AEAs may change. For example, at a first time period, the user may be holding a device so that his/her skin is in contact with the electrode tiles in the first AEA 1305-a-1 and the second AEA 1305-a-2. The electrode tiles in these AEAs may collect electrodermal data associated with the user while they are activated (i.e., in contact with the user's skin). At a second time period, the user may change the position of his/her grip of the device. As a result, the user may no longer be in contact with the electrode tiles in the first AEA 1305-a-1. These electrode tiles may therefore be deactivated and the first AEA 1305-a-1 may cease to exist. Electrodermal data may still be collected during the second time period via the electrode tiles of the second AEA 1305-a-2, if the user continues to touch this portion of the array 260-e. If the user grips a previously untouched portion of the array 260-e, the electrode tiles in this portion may be coupled and a new AEA may be formed.

As illustrated in this example, the AEAs may be dynamically changed, and the biopotential electrode array 260-e may be dynamically configured. For example, as the user shifts his/her grip on the surface area 955-c, which is an example of the surface area 955 of the device 115-c shown in FIGS. 9, 10, and/or 11, the position and number of AEAs may also change. In one embodiment, the polling module 605 (FIG. 6) may continuously poll the flow of current between adjacent electrode tiles to determine which contiguous areas remain active and which inactive areas of the array 260-e should be activated. This architecture allows the collection of the electrodermal data to occur while the user adjusts his/her grip on a device such as the device 115-c (as long as at least a portion of the skin is contacting the array 260-e).

Figure 14:
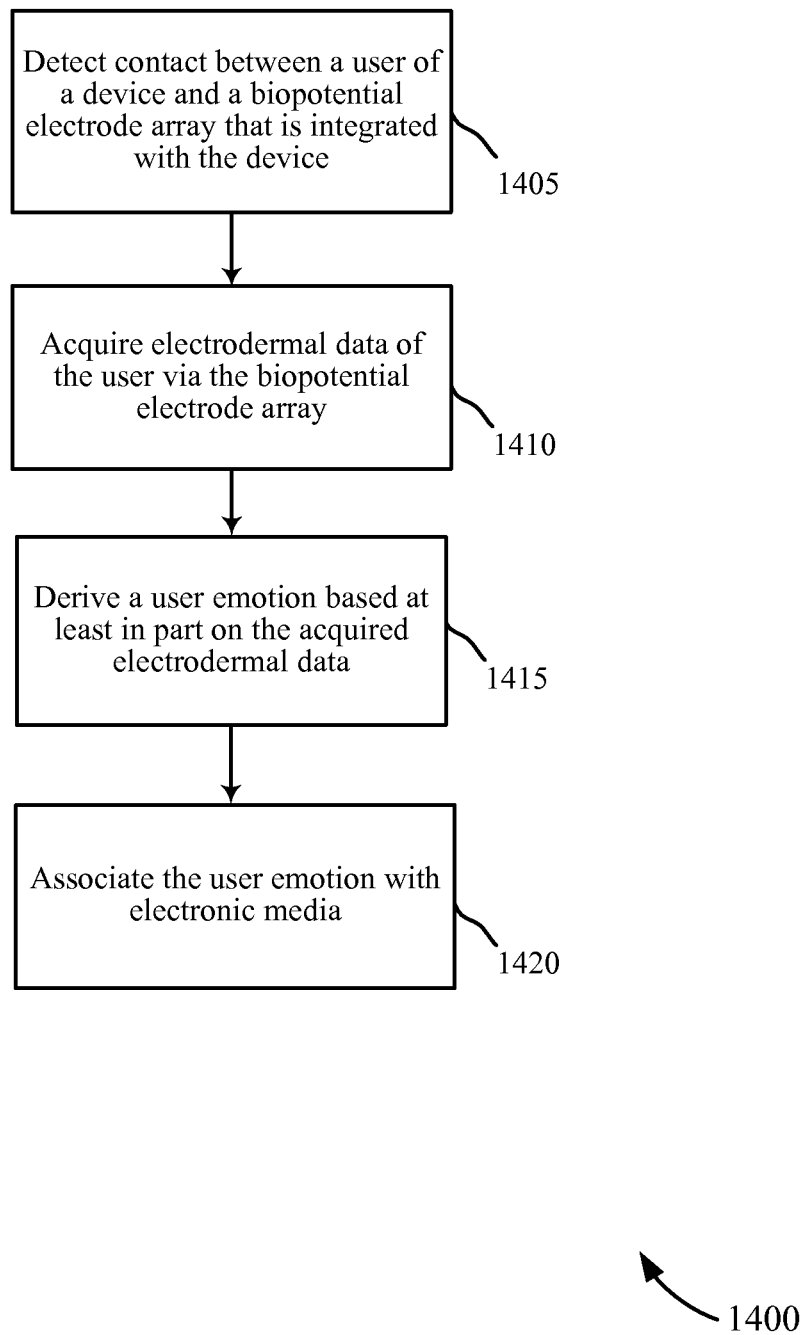
FIG. 14 is a flow chart of a first example of a method for associating user emotion with electronic media.

Referring now to FIG. 14, a flow chart is provided illustrating one example of a method 1400 for associating user emotion with electronic media. The method 1400 may be implemented by a device, such as the mobile device 115 of FIGS. 1, 2, 3, and/or 9. In one configuration, the method 1400 may be implemented by the emotion processing module 265 of FIGS. 2 and/or 3.

At block 1405, contact is detected between a user of a device and a biopotential electrode array that is integrated with the device. The biopotential electrode array may in some cases be one of the biopotential electrode arrays 260 shown in FIGS. 2, 3, 4, 5, 6, 9, 10, 11, 12, and/or 13.

At block 1410, electrodermal data of the user is acquired via the biopotential electrode array. The acquisition may in some cases involve dynamically configuring the biopotential electrode array, and in some cases may result in the generation of an SCR.

In one configuration, at block 1415, user emotion is derived, at least in part, based on the acquired electrodermal data. The user emotion may then be associated with electronic media at block 1420. In some cases, the electronic media may be an image, video, audio recording, or web page.

Therefore, the method 1400 may provide for associating user emotion with electronic media, using a biopotential electrode array integrated with a device such as the mobile device 115. It should be noted that the method 1400 is just one implementation and that operations of the method 1400 may be rearranged or otherwise modified such that other implementations are possible.

Figure 15:
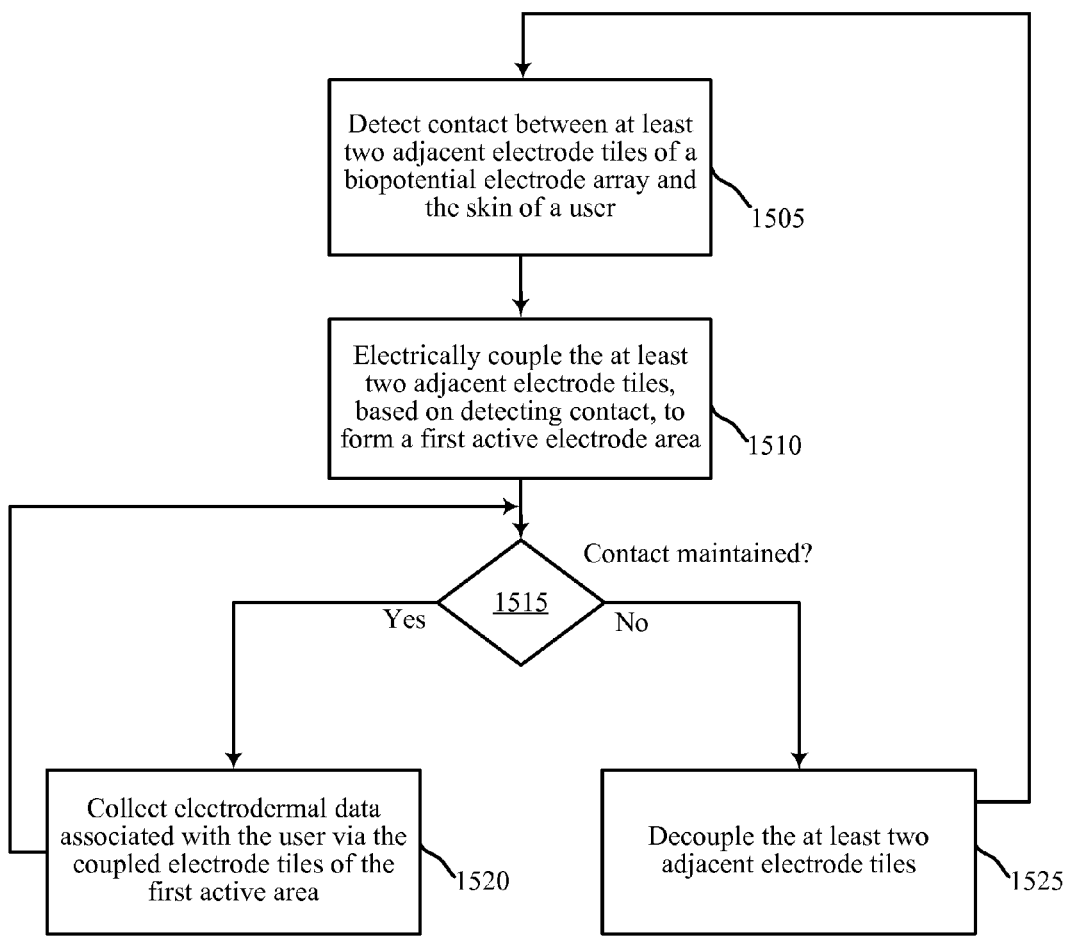
FIG. 15 is a flow chart of an example method for detecting contact between a user of a device and a dynamically configurable biopotential electrode array.

FIG. 15 is an example of a method 1500 to detect contact between a user of a device and a dynamically configurable biopotential electrode array, to determine whether to maintain an electric coupling of at least two electrode tiles within the biopotential electrode array, and to acquire electrodermal data of the user via the biopotential electrode array. The method 1500 may in some cases be employed to accomplish the detecting and acquiring actions of the methods shown in FIGS. 14 and 17. The method 1500 may be implemented by a device, such as the mobile device 115 of FIG. 1, 2, 3 and/or 9. In some configurations, the method 1500 may be implemented by the emotion processing module 265 of FIGS. 2 and/or 3, or by the detection module 310 and acquisition module 315 of FIGS. 3, 4, 5, and/or 6.

In one example, the biopotential electrode array (including a number of electrode tiles) may be included on an external portion of the mobile device 115. At block 1505, contact between at least two adjacent electrode tiles and skin of a user may be detected. At block 1510, the at least two adjacent electrode tiles may be coupled when contact is detected. The coupled electrode tiles may form a first AEA. In one configuration, at block 1515, a determination may be made as to whether the contact between the user's skin and the electrode tiles is maintained. For example, the polling module 605 may poll the coupled electrode tiles to determine whether the flow of current between the electrodes is greater than zero. If it is determined that the contact is maintained (i.e., flow of current is greater than zero), electrodermal data may be collected by the coupled electrode tiles of the first AEA at block 1520. The electrode tiles may include biosensors to collect the data. The method 1500 may then return to determine whether the contact persists by continuing to poll the coupled electrode tiles. If, however, it is determined that the contact is terminated, the at least two adjacent electrode tiles may be decoupled at block 1525. The uncoupled electrode tiles may cease to collect electrodermal data associated with the user. The method 1500 may then return to continue to detect whether adjacent electrode tiles are in contact with the user's skin.

Therefore, the method 1500 may determine whether contact is maintained between electrode tiles and the skin of the user. It should be noted that the method 1500 is just one implementation and that operations of the method 1500 may be rearranged or otherwise modified such that other implementations are possible.

Figure 16:
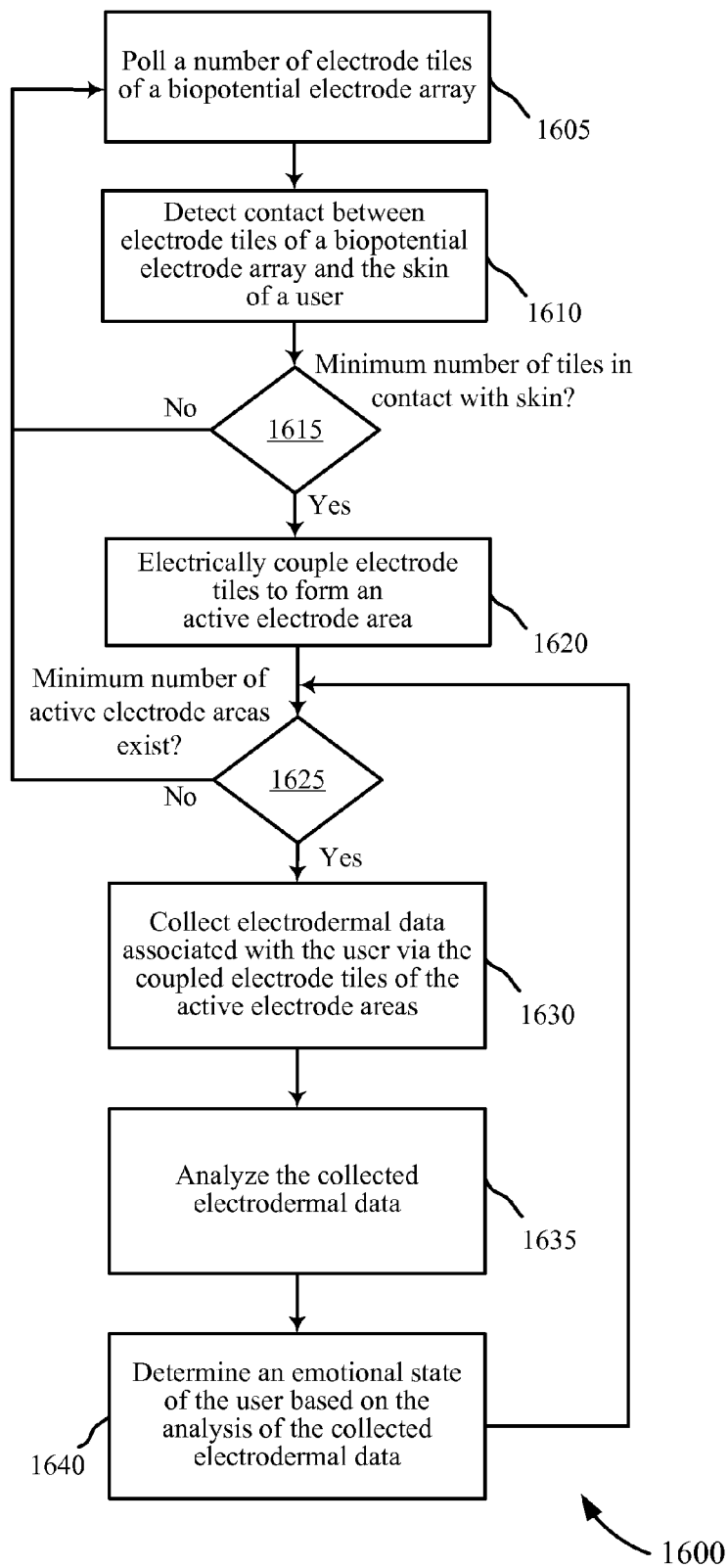
FIG. 16 is a flow chart of an example method for polling electrode tiles of a dynamically configurable biopotential electrode array to detect contact between the skin of a user and at least two of the electrode tiles.

Referring now to FIG. 16, a flow chart illustrates one example of a method 1600 to poll electrode tiles of a dynamically configurable biopotential electrode array to detect contact between the skin of a user and at least two of the electrode tiles. The method 1600 may in some cases be employed to accomplish the detecting, acquiring and deriving actions of the methods shown in FIGS. 14 and 17. The method 1600 may be implemented by a device, such as the mobile device 115 of FIGS. 1, 2, 3 and/or 9. In some configurations, the method 1600 may be implemented by the emotion processing module 265 of FIGS. 2 and/or 3, or by the detection module 310 and acquisition module 315 of FIGS. 3, 4, 5, and/or 6.

At block 1605, a number of electrode tiles of a biopotential electrode array may be polled. For example, the current flow between adjacent electrode tiles may be polled to determine whether the flow is greater than zero. In one configuration, the array may be embedded on an external surface area of the mobile device 115. At block 1610, contact between electrode tiles and the skin of a user of the mobile device 115 may be detected. At block 1615, a determination may be made as to whether a minimum number of electrode tiles are in contact with the skin. If it is determined that a minimum number of electrode tiles are not in contact with the user's skin, the method 1600 may return to continue to poll electrode tiles to detect contact. If, however, it is determined that a minimum number of electrode tiles are in contact with the skin, at block 1620, the electrode tiles in contact with the skin may be electrically coupled to form an AEA.

At block 1625, a determination may be made as to whether a minimum number of AEAs exist. For example, certain types of electrodermal data may be gathered from a minimum number of AEAs. As an example, to collect SCR data, at least two AEAs may be used. If it is determined that a minimum number of AEAs do not exist to collect the desired electrodermal data, the method 1600 may return to poll electrodes within the array to detect contact. If, however it is determined that a minimum number of AEAs exist, at block 1630, the electrodermal data may be collected via the electrode tiles of the AEAs. While the data is being collected, the polling module 605 may continue to poll electrode tiles in real time in order to detect whether the contact is maintained between the currently coupled electrode tiles as well as whether contact is detected between the skin and previously uncoupled electrode tiles.

At block 1635, the collected data may be analyzed. At block 1640, a state of the user may be determined based on the analysis. For example, an emotional state of the user may be determined based on the analyzed electrodermal data. The method 1600 may return to determine whether the minimum number of AEAs still exists. If the AEAs are maintained, electrodermal data may continue to be collected via biosensors associated with the electrode tiles in the AEAs.

Therefore, the method 1600 may poll electrode tiles of a dynamically configurable biopotential electrode array to detect contact between skin of a user and the electrode tiles. It should be noted that the method 1600 is just one implementation and that operations of the method 1600 may be rearranged or otherwise modified such that other implementations are possible.

As provided by the description above, a biopotential electrode array of electrode tiles may be embedded on an external surface area of the mobile device 115. The electrode tiles may be associated with biosensors used to collect electrodermal data relating to a user of the mobile device 115. The electrode tiles may be decoupled from each other until they come into contact with the user's skin. Decoupled electrode tiles may not be activated to collect electrodermal data associated with a user of the device 115. When contact is detected, an electronic switch between adjacent electrode tiles may close, thus electrically coupling the electrode tiles in contact with the skin. The biosensors associated with these coupled electrode tiles may then begin to collect electrodermal data about the user. As the user changes his/her grip of the mobile device 115 and touches different portions of the array, the coupled electrode tiles may be decoupled if contact with the skin does not persist. Previously uncoupled electrode tiles, that may now be in contact with the skin, may be electrically coupled to begin collecting the data.

Figure 17:
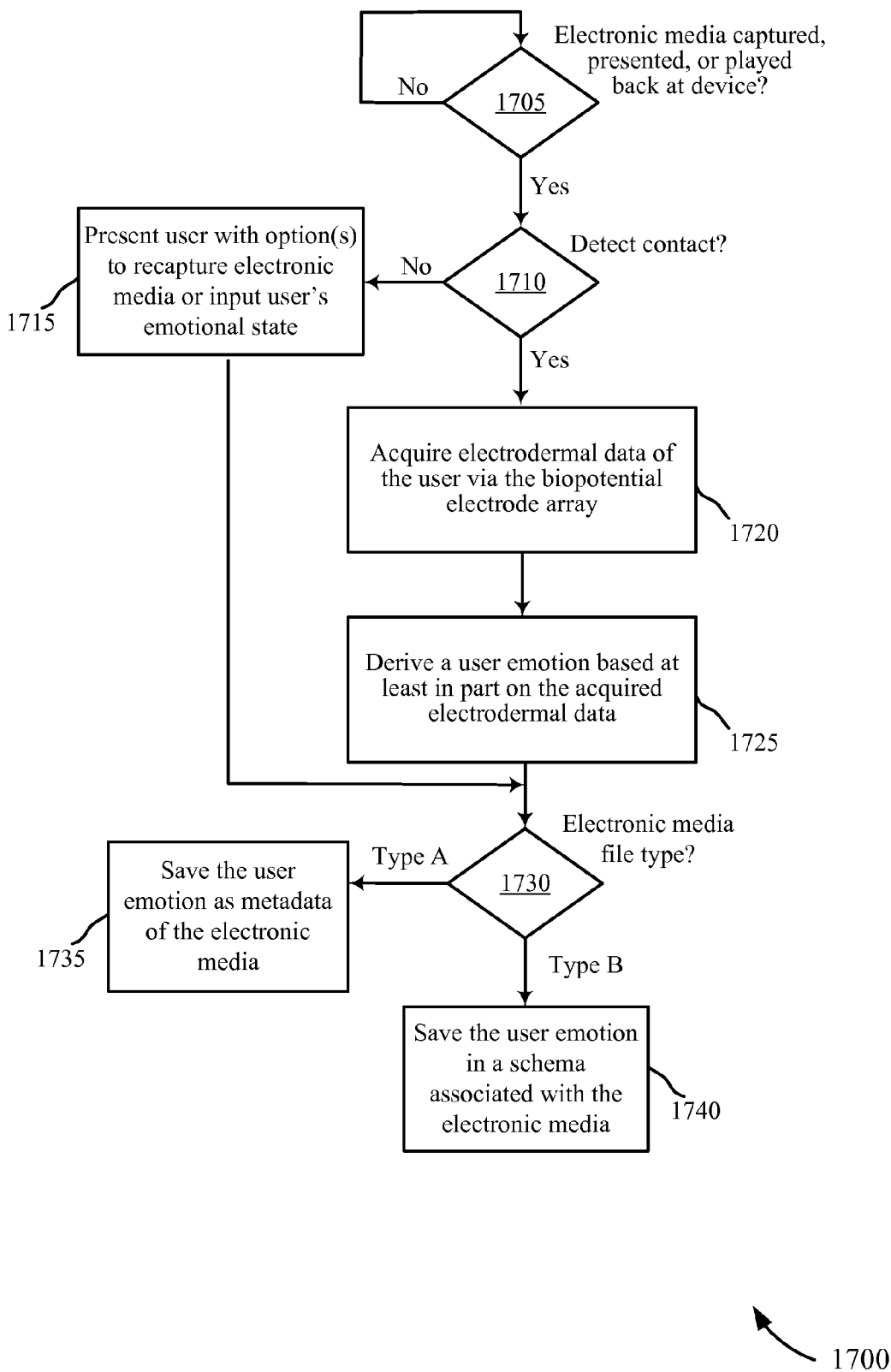
FIG. 17 is a flow chart of a second example of a method for associating user emotion with electronic media.

Referring now to FIG. 17, a flow chart is provided illustrating another example of a method 1700 for associating user emotion with electronic media. The method 1700 may be implemented by a device, such as the mobile device 115 of FIGS. 1, 2, 3, and/or 9. In one configuration, the method 1700 may be implemented by the emotion processing module 265 of FIGS. 2 and/or 3.

At block 1705, it is determined whether electronic media is being captured, presented, or played back. In some embodiments, this may include detecting a device's capture of electronic media using, for example, a camera, microphone, or communications interface. The capturing may be detected, for example, by detecting activation or use of camera or media recording hardware, by detecting an orientation of the device with respect to gravity (e.g., a landscape orientation, typical of camera use), by detecting activation or use of a camera or media recording application installed on the device, or by detecting a signal indicative of an image, video, or audio recording having been captured (e.g., activation of a button or icon that causes an image, video or audio clip to be captured/recorded).

In the same or other embodiments, a determination that electronic media is being played back by a device may be made, for example, by detecting activation or use of a media play back application installed on the device. A determination that electronic media is being presented to a user may be made in a similar manner. Media presentation may also be detected by virtue of media content being displayed via a web browser.

The operations performed at block 1705 may in some cases involve communication between the emotion processing module 265, media capture module 240, media presentation module 245, media play back module 250, web browser module 255, and/or other modules or components of the device 115-*a* shown in FIG. 2.

At block 1710, and upon determining that electronic media is being captured, presented, or played back by a device, it is determined whether there is contact between a user of the device and a biopotential electrode array that is integrated with the device. If contact is detected, electrodermal data of the user is acquired via the biopotential electrode array at block 1720. In some cases, the acquisition of electrodermal data may include dynamically configuring the biopotential electrode array to acquire the electrodermal data. The operations performed at blocks 1710 and 1720 may in some cases be performed using part or all of the method 1500 or 1600.

At block 1725, user emotion is derived. The user emotion is based at least in part on the acquired electrodermal data. The operation performed at block 1725 may in some cases be performed using part of the method 1600 (e.g., blocks 1635 and 1640).

When sufficient contact between the device user and the biopotential electrode array does not exist (i.e., the answer is "No" at block 1710), the device user may be presented with one or more options, such as an option to recapture the electronic media, or an option to input the user's emotion. These options may be provided via a user interface (e.g., a graphical user interface) of the device. In some cases, an indicator of a default or best guess user emotion may be presented to the user via the user interface.

At block 1730, the "type" or "file type" of the electronic media with which user emotion is being associated is determined. As previously discussed, the media type may be, for example: image, video, or audio. The media file type may be, for example: JPEG, TIFF, or another file format used to store electronic media.

Based on the determination made at block 1730, the user emotion may be associated with the electronic media by saving the user emotion as metadata of the electronic media (at block 1735) or saving the user emotion in a schema associated with the electronic media (at block 1740).

In some embodiments of the systems, methods, devices, and apparatuses disclosed herein, the systems, methods, devices, and apparatuses are automated (or substantially automated). Automation helps ensure that user emotion is routinely associated with electronic media.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A method of associating a user emotion with electronic media, comprising:
   detecting contact between a user of a device and a biopotential electrode array that is integrated with the device;
   detecting, by the device, that the electronic media is being at least one of captured by, played back to, presented to, or combinations thereof, the user;
   acquiring electrodermal data of the user via the biopotential electrode array based at least in part on detecting that the electronic media is being at least one of captured by, presented to, played back to, or combinations thereof, the user;
   deriving the user emotion based at least in part on the acquired electrodermal data;
   associating the derived user emotion with the electronic media that has been at least one of captured, presented, played back, or combinations thereof.

2. The method of claim 1, wherein detecting the contact between the user of the device and the biopotential electrode array is based at least partly in response to detecting the capturing.

3. The method of claim 1, wherein detecting the contact between the user of the device and the biopotential electrode array is based at least partly in response to detecting the play back.

4. The method of claim 1, wherein detecting the contact between the user of the device and the biopotential electrode array is based at least partly in response to detecting the presentation.

5. The method of claim 1, further comprising:
   detecting activation of an application installed on the device;
   wherein detecting the contact between the user of the device and the biopotential electrode array is based at least partly in response to detecting the activation.

6. The method of claim 5, wherein the application is a camera application.

7. The method of claim 1, further comprising:
   detecting an orientation of the device with respect to gravity;
   wherein detecting the contact between the user of the device and the biopotential electrode array is based at least partly in response to detecting the orientation.

8. The method of claim 7, wherein the orientation is a landscape orientation.

9. The method of claim 1, wherein acquiring the electrodermal data comprises:
   dynamically configuring the biopotential electrode array based at least in part on electrode tiles of the biopotential electrode array that are electrically detected to be in contact with skin of the user; and
   acquiring the electrodermal data from the configured biopotential electrode array.

10. The method of claim 9, wherein dynamically configuring the biopotential electrode array comprises:
    electrically coupling at least two adjacent electrode tiles to form a first active electrode area within the biopotential electrode array.

11. The method of claim 1, wherein deriving the user emotion comprises:
    correlating the electrodermal data with one of a plurality of emotional states.

12. The method of claim 1, wherein associating the derived user emotion with the electronic media comprises:
    saving the derived user emotion as metadata of the electronic media.

13. The method of claim 1, wherein associating the derived user emotion with the electronic media comprises:
    saving the user emotion in a schema associated with the electronic media.

14. The method of claim 1, further comprising:
    presenting, on the device, a user interface to edit the user emotion.

15. The method of claim 1, wherein the electronic media is an image.

16. The method of claim 1, wherein the electronic media is a video.

17. The method of claim 1, wherein the electronic media is an audio recording.

18. The method of claim 1, wherein the device is a mobile phone.

19. The method of claim 1, wherein the device is a camera.

20. The method of claim 1, wherein the biopotential electrode array comprises:
    a group of electrodes positioned at a corner of the device, on at least a side edge of the device.

21. The method of claim 1, wherein the biopotential electrode array comprises:
    a plurality of groups of electrodes, each group of electrodes being positioned at a different one of four corners of the device, and each group of electrodes being positioned on at least a side edge of the device.

22. A device for associating a user emotion with electronic media, comprising:
    a processor;
    memory in electronic communication with the processor; and
    instructions stored in the memory, the instructions being executable by the processor to:
      detect contact between a user of the device and a biopotential electrode array that is integrated with the device;
      detect, by the device, that the electronic media is being at least one of captured by, played back to, presented to, or combinations thereof, the user;
      acquire electrodermal data of the user via the biopotential electrode array based at least in part on detecting that the electronic media is being at least one of captured by, presented to, played back to, or combinations thereof, the user;
      derive the user emotion based at least in part on the acquired electrodermal data;
    associate the derived user emotion with the electronic media that has been at least one of captured, presented, played back, or combinations thereof.

23. The device of claim 22, wherein the instructions are further executable by the processor to:
    detect contact between the user of the device and the biopotential electrode array based at least partly in response to detecting the capturing.

24. The device of claim 22, wherein the instructions are further executable by the processor to:
    detect contact between the user of the device and the biopotential electrode array based at least partly in response to detecting the play back.

25. The device of claim 22, wherein the instructions are further executable by the processor to:

detect contact between the user of the device and the biopotential electrode array based at least partly in response to detecting the presentation.

26. The device of claim 22, wherein the instructions to associate the derived user emotion with the electronic media comprise instructions to:
save the derived user emotion as metadata of the electronic media.

27. The device of claim 22, wherein the instructions to associate the derived user emotion with the electronic media comprise instructions to:
save the user emotion in a schema associated with the electronic media.

28. The device of claim 22, further comprising the biopotential electrode array, wherein the biopotential electrode array comprises:
a group of electrodes positioned at a corner of the device, on at least a side edge of the device.

29. The device of claim 22, further comprising the biopotential electrode array, wherein the biopotential electrode array comprises:
a plurality of groups of electrodes, each group of electrodes being positioned at a different one of four corners of the device, and each group of electrodes being positioned on at least a side edge of the device.

30. An apparatus for associating a user emotion with electronic media, comprising:
means for detecting contact between a user of a device and a biopotential electrode array that is integrated with the device;
means for detecting, by the device, that the electronic media is being at least one of captured by, played back to, presented to, or combinations thereof, the user;
means for acquiring electrodermal data of the user via the biopotential electrode array based at least in part on detecting that the electronic media is being at least one of captured by, presented to, played back to, or combinations thereof, the user;
means for deriving the user emotion based at least in part on the acquired electrodermal data;
means for associating the derived user emotion with the electronic media that has been at least one of captured, presented, played back, or combinations thereof.

31. The apparatus of claim 30, wherein the means for detecting the contact between the user of the device and the biopotential electrode array detects the contact at least partly in response to detecting the capturing.

32. The apparatus of claim 30, wherein the means for detecting the contact between the user of the device and the biopotential electrode array detects the contact at least partly in response to detecting the play back.

33. The apparatus of claim 30, wherein the means for detecting the contact between the user of the device and the biopotential electrode array detects the contact at least partly in response to detecting the presentation.

34. The apparatus of claim 30, wherein the means for associating the derived user emotion with the electronic media comprises:
means for saving the derived user emotion as metadata of the electronic media.

35. The apparatus of claim 30, wherein the means for associating the derived user emotion with the electronic media comprises:
means for saving the user emotion in a schema associated with the electronic media.

36. A computer program product for associating a user emotion with electronic media, the computer program product comprising a non-transitory computer-readable medium storing instructions executable by a processor to:
detect contact between a user of a device and a biopotential electrode array that is integrated with the device;
detect, by the device, that the electronic media is being at least one of captured by, played back to, presented to, or combinations thereof, the user;
acquire electrodermal data of the user via the biopotential electrode array based at least in part on detecting that the electronic media is being at least one of captured by, presented to, played back to, or combinations thereof, the user;
derive the user emotion based at least in part on the acquired electrodermal data;
associate the derived user emotion with the electronic media that has been at least one of captured, presented, played back, or combinations thereof.

* * * * *